US012740730B2

(12) United States Patent
Bechtel et al.

(10) Patent No.: US 12,740,730 B2
(45) Date of Patent: *Sep. 22, 2026

(54) WIRELESS OXIMETER PROBE WITH ELONGATED TUBE

(71) Applicant: ViOptix, Inc., Newark, CA (US)

(72) Inventors: Kate LeeAnn Bechtel, Pleasant Hill, CA (US); Todd Louis Harris, Fremont, CA (US); Edward Gerald Solomon, Menlo Park, CA (US); Winston Sun, San Jose, CA (US); Alan Baldwin, San Jose, CA (US); Scott E. Coleridge, New York, NY (US); Mark Lonsinger, San Jose, CA (US)

(73) Assignee: ViOptix, Inc., Newark, CA (US)

(*) Notice: Subject to any disclaimer, the term of this patent is extended or adjusted under 35 U.S.C. 154(b) by 26 days.

This patent is subject to a terminal disclaimer.

(21) Appl. No.: 18/582,559

(22) Filed: Feb. 20, 2024

(65) Prior Publication Data

US 2024/0188861 A1 Jun. 13, 2024

Related U.S. Application Data

(63) Continuation of application No. 17/002,730, filed on Aug. 25, 2020, now Pat. No. 11,903,703, which is a (Continued)

(51) Int. Cl.
*A61B 5/1455* (2006.01)
*A61B 1/00* (2006.01)
(Continued)

(52) U.S. Cl.
CPC ........ *A61B 5/1459* (2013.01); *A61B 1/00006* (2013.01); *A61B 1/00016* (2013.01);
(Continued)

(58) Field of Classification Search
CPC . A61B 5/0205; A61B 5/1455; A61B 5/14551; A61B 5/14552; A61B 5/1459;
(Continued)

(56) References Cited

U.S. PATENT DOCUMENTS 5,830,137 A 11/1998 Scharf
6,850,789 B2 2/2005 Schweitzer et al.
(Continued)

*Primary Examiner* — Chu Chuan Liu
(74) *Attorney, Agent, or Firm* — Aka Chan LLP

(57) ABSTRACT

A laparoscopic medical device includes an oximeter sensor at its tip, which allows the making of oxygen saturation measurements laparoscopically. The device can be a unitary design, wherein a laparoscopic element includes electronics for the oximeter sensor at a distal end (e.g., opposite the tip). The device can be a multiple piece design (e.g., two-piece design), where some electronics is in a separate housing from the laparoscopic element, and the pieces (or portions) are removably connected together. The laparoscopic element can be removed and disposed of; so, the electronics can be reused multiple times with replacement laparoscopic elements. The electronics can include a processing unit for control, computation, or display, or any combination of these. However, in an implementation, the electronics can connect wirelessly to other electronics (e.g., another processing unit) for further control, computation, or display, or any combination of these.

35 Claims, 28 Drawing Sheets

Related U.S. Application Data continuation of application No. 15/652,638, filed on Jul. 18, 2017, now Pat. No. 10,750,986.

(60) Provisional application No. 62/363,562, filed on Jul. 18, 2016.

(51) Int. Cl.

| | |
|---|---|
| ***A61B 1/313*** | (2006.01) |
| ***A61B 5/00*** | (2006.01) |
| ***A61B 5/0205*** | (2006.01) |
| ***A61B 5/1459*** | (2006.01) |
| *A61B 5/145* | (2006.01) |
| *A61B 5/1495* | (2006.01) |

(52) U.S. Cl.

CPC ...... *A61B 1/00032* (2013.01); *A61B 1/00052* (2013.01); *A61B 1/00087* (2013.01); *A61B 1/00105* (2013.01); *A61B 1/00108* (2013.01); *A61B 1/00126* (2013.01); *A61B 1/00154* (2013.01); *A61B 1/00181* (2013.01); *A61B 1/313* (2013.01); *A61B 5/0004* (2013.01); *A61B 5/0015* (2013.01); *A61B 5/0205* (2013.01); *A61B 5/14551* (2013.01); *A61B 5/14552* (2013.01); *A61B 5/7225* (2013.01); *A61B 5/7278* (2013.01); *A61B 5/742* (2013.01); *A61B 1/0005* (2013.01); *A61B 1/00142* (2013.01); *A61B 5/0071* (2013.01); *A61B 5/14546* (2013.01); *A61B 5/1495* (2013.01); *A61B 5/6852* (2013.01); *A61B 5/7445* (2013.01); *A61B 2505/05* (2013.01); *A61B 2560/0214* (2013.01); *A61B 2560/0223* (2013.01); *A61B 2560/0443* (2013.01)

(58) Field of Classification Search

CPC ... A61B 5/0004; A61B 5/0015; A61B 5/7278; A61B 5/742; A61B 5/7225; A61B 5/6852; A61B 5/1495; A61B 5/7445; A61B 5/14546; A61B 1/00064; A61B 1/00066; A61B 1/00071; A61B 1/0008; A61B 1/00087; A61B 1/00096; A61B 1/00097; A61B 1/000121; A61B 1/000124; A61B 1/000126

See application file for complete search history.

(56) References Cited

U.S. PATENT DOCUMENTS

| | | | |
|---|---|---|---|
| 7,729,735 | B1 | 6/2010 | Burchman |
| 2005/0049471 | A1 | 3/2005 | Aceti |
| 2005/0277818 | A1 | 12/2005 | Myers |
| 2007/0244363 | A1 | 10/2007 | Sano et al. |
| 2008/0319290 | A1 | 12/2008 | Mao et al. |
| 2011/0077473 | A1 | 3/2011 | Lisogurski |
| 2011/0112387 | A1 | 5/2011 | Li et al. |
| 2011/0130632 | A1 | 6/2011 | Mcgrail et al. |
| 2011/0245633 | A1 | 10/2011 | Goldberg et al. |
| 2012/0289801 | A1 | 11/2012 | Yamaguchi |
| 2013/0060109 | A1 | 3/2013 | Besko et al. |
| 2014/0046152 | A1 | 2/2014 | Bechtel et al. |

TOWER-MOUNTED DISPLAY
DISPLAY ELEMENT 115
WIRED OR WIRELESS TRANSMITTER 490
BATTERY 430
POWER SUPPLY 435
PROCESSOR 420
MEMORY 422
LIGHT ENGINE 440
ADCs 465
TIAs 460
PHOTODIODES 455
OPTICAL PORT
COUPLER ELEMENT
COUPLER ELEMENT
OPTICAL PORT
TROCAR
TROCAR
ABDOMINAL WALL
ABDOMINAL WALL
INSUFFLATED BODY CAVITY
INSUFFLATED BODY CAVITY
LAPAROSCOPIC TUBE 452
SENSOR HEAD
TISSUE UNDER TEST
400
401
415
417
419
445
447
449
450
450
457
464
464
467
478
480
485

FIG. 6

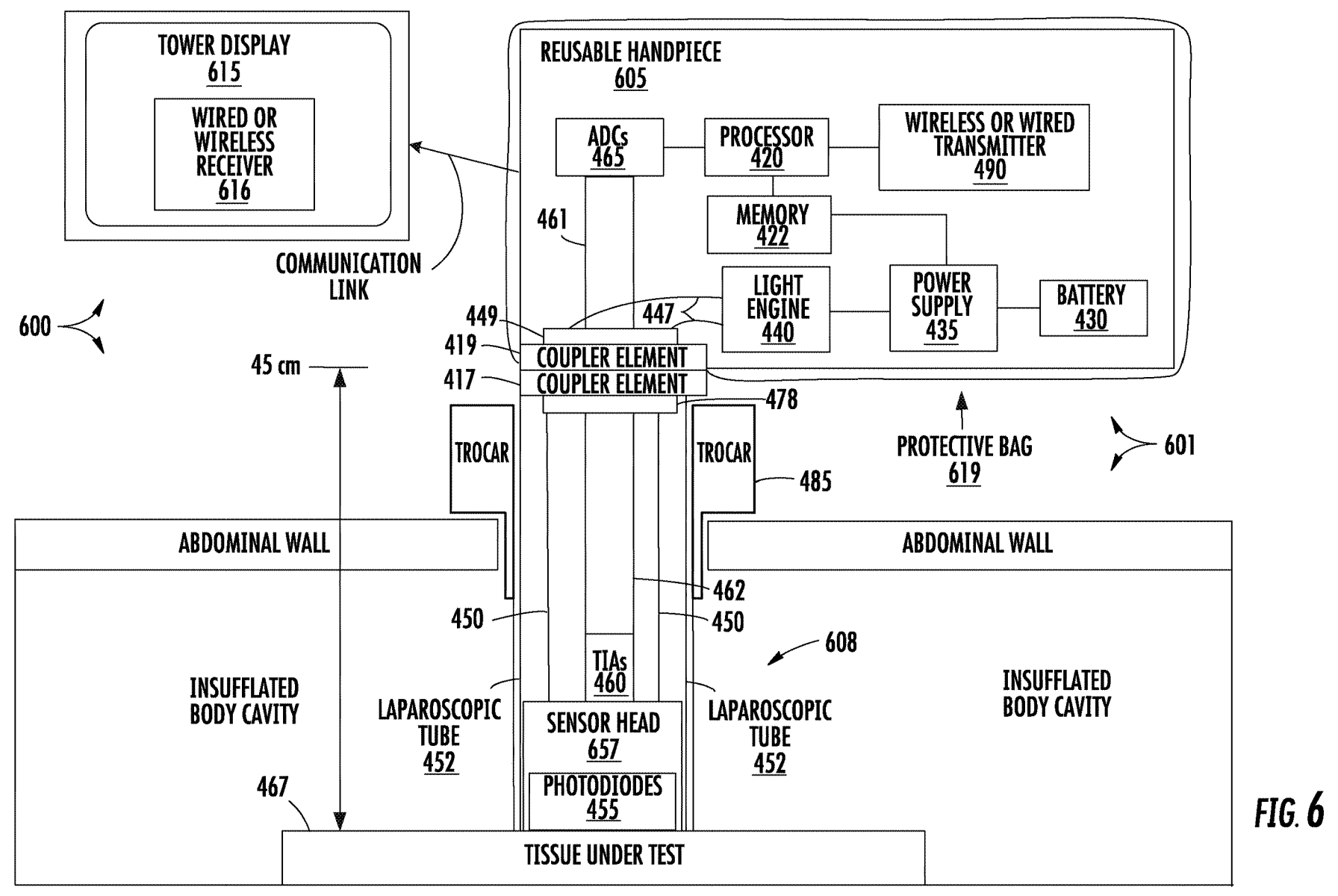

REUSABLE HANDPIECE 605
PROCESSOR 420
WIRELESS OR WIRED TRANSMITTER 490
MEMORY 422
POWER SUPPLY 435
BATTERY 430
LIGHT ENGINE 440
ADCs 465
461
447
COUPLER ELEMENT
COUPLER ELEMENT
449
419
417
478
601
PROTECTIVE BAG 619
TROCAR
TROCAR
485
ABDOMINAL WALL
ABDOMINAL WALL
INSUFFLATED BODY CAVITY
INSUFFLATED BODY CAVITY
608
462
450
450
LAPAROSCOPIC TUBE 452
LAPAROSCOPIC TUBE 452
TIAs 460
SENSOR HEAD 657
PHOTODIODES 455
TISSUE UNDER TEST
467
45 cm
COMMUNICATION LINK
TOWER DISPLAY 615
WIRED OR WIRELESS RECEIVER 616
600

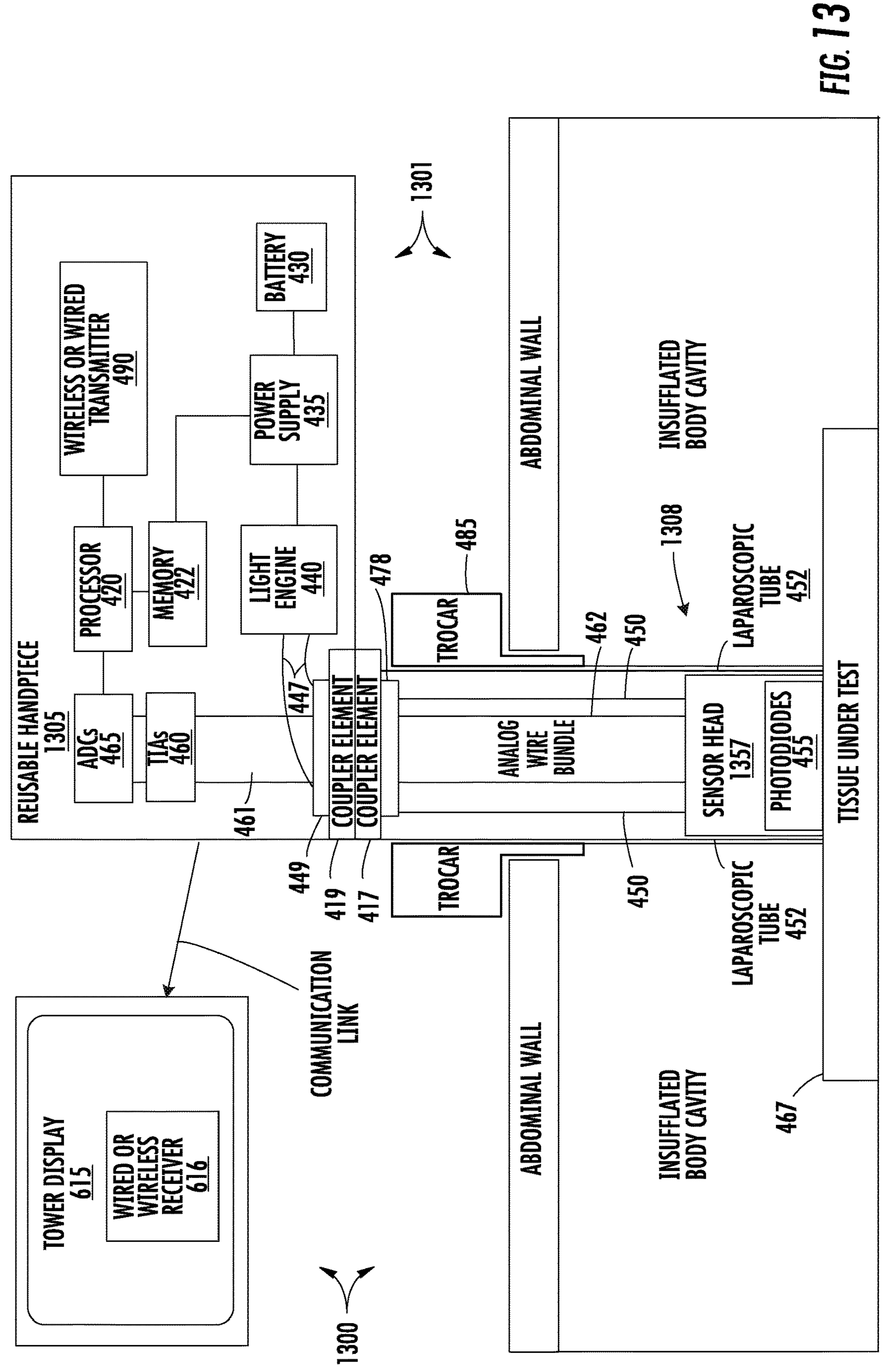
FIG. 13
1301
1300
REUSABLE HANDPIECE 1305
ADCs 465
TIAs 460
PROCESSOR 420
MEMORY 422
LIGHT ENGINE 440
WIRELESS OR WIRED TRANSMITTER 490
POWER SUPPLY 435
BATTERY 430
461
447
COUPLER ELEMENT
COUPLER ELEMENT
449
419
417
478
TROCAR
485
TROCAR
ABDOMINAL WALL
ABDOMINAL WALL
INSUFFLATED BODY CAVITY
INSUFFLATED BODY CAVITY
1308
LAPAROSCOPIC TUBE 452
LAPAROSCOPIC TUBE 452
462
450
450
ANALOG WIRE BUNDLE
SENSOR HEAD 1357
PHOTODIODES 455
TISSUE UNDER TEST
467
COMMUNICATION LINK
TOWER DISPLAY 615
WIRED OR WIRELESS RECEIVER 616

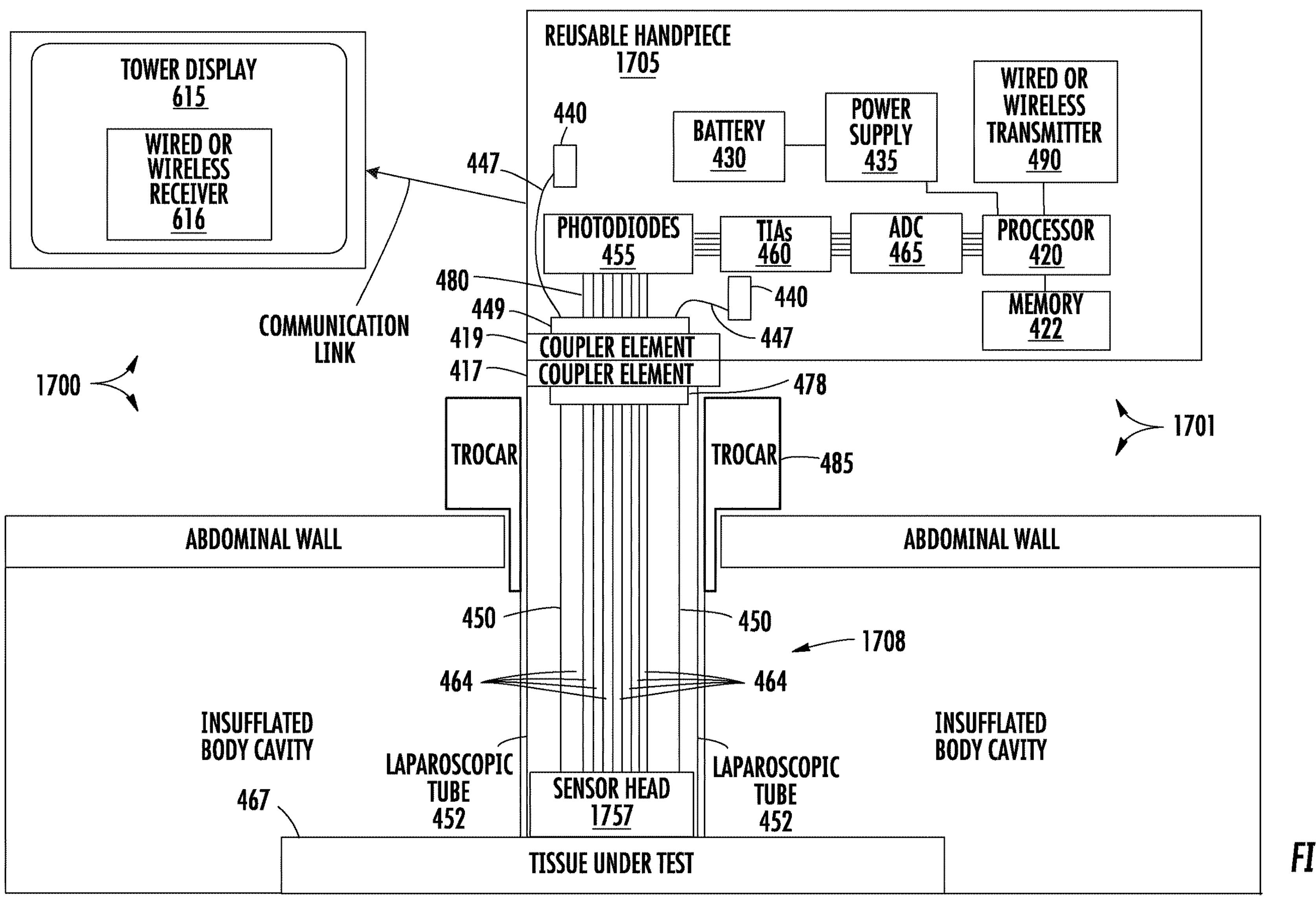
TOWER DISPLAY 615
WIRED OR WIRELESS RECEIVER 616
REUSABLE HANDPIECE 1705
440
447
BATTERY 430
POWER SUPPLY 435
WIRED OR WIRELESS TRANSMITTER 490
PHOTODIODES 455
TIAs 460
ADC 465
PROCESSOR 420
MEMORY 422
480
449
419
417
COUPLER ELEMENT
COUPLER ELEMENT
440
447
478
COMMUNICATION LINK
1700
1701
TROCAR
TROCAR
485
ABDOMINAL WALL
ABDOMINAL WALL
450
450
1708
464
464
INSUFFLATED BODY CAVITY
LAPAROSCOPIC TUBE 452
SENSOR HEAD 1757
LAPAROSCOPIC TUBE 452
INSUFFLATED BODY CAVITY
467
TISSUE UNDER TEST
FIG. 17

DISPLAY
2115
MEMORY
422
PROCESSOR
420
WIRED OR WIRELESS
RECEIVER
616
COMMUNICATION
LINK
2200

WIRED OR WIRELESS
TRANSMITTER
490
PREPROCESSOR
(FPGA OR CPLD)
520
POWER
SUPPLY
435
ADCs
465
BATTERY
430
TIAs
460
440
455
2201
PROBE UNIT
2105
LAPAROSCOPIC
ELEMENT
2108
450
464
SENSOR HEAD

WIRELESS OXIMETER PROBE WITH ELONGATED TUBE

CROSS-REFERENCE TO RELATED APPLICATIONS

This application is a continuation of U.S. patent application Ser. No. 17/002,730, filed Aug. 25, 2000, issued as U.S. Pat. No. 11,903,703 on Feb. 20, 2024, which is a continuation of U.S. patent application Ser. No. 15/652,638, filed Jul. 18, 2017, issued as U.S. Pat. No. 10,750,986 on Aug. 25, 2020, which claims the benefit of U.S. patent application 62/363,562 filed Jul. 18, 2016. These applications are incorporated by reference along with all other references cited in this application.

BACKGROUND OF THE INVENTION

The invention relates generally to optical systems that monitor oxygen levels in tissue. More specifically, the invention relates to optical probes, such as oximeters, that include source structures and detector structures on a tip of a laparoscopic probe.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or person training for a marathon); and veterinary purposes (e.g., animal monitoring).

Pulse oximeters and tissue oximeters are two types of oximeters that operate on different principles. A pulse oximeter uses a pulse to make measurements. A pulse oximeter typically measures the absorbance of light due to pulsing arterial blood. In contrast, a tissue oximeter does not need a pulse in order to function, and can be used to make oxygen saturation measurements of a tissue flap that has been disconnected from a blood supply or of tissue, such as internal organs that are connected to a blood supply.

Human tissue, as an example, includes a variety of light-absorbing molecules. Such chromophores include oxygenated hemoglobin, deoxygenated hemoglobin, melanin, water, lipid, and cytochrome. Oxygenated hemoglobin, deoxygenated hemoglobin, and melanin are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving form factor; improving measurement accuracy; reducing measurement time; lowering cost; reducing size, weight, or form factor; reducing power consumption; and for other reasons, and any combination of these measurements.

In particular, assessing a patient's oxygenation state, at both the regional and local level, is important as it is an indicator of the state of the patient's local tissue health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of nonideal conditions. While existing oximeters have been sufficient for postoperative tissue monitoring where absolute accuracy is not critical and trending data alone is sufficient, accuracy is, however, important during surgery in which spot-checking can be used to determine whether tissue might remain viable or needs to be removed.

Therefore, there is a need for improved tissue oximeter probes and methods of making measurements using these probes.

BRIEF SUMMARY OF THE INVENTION

A laparoscopic medical device includes an oximeter sensor at its tip, which allows the making of oxygen saturation measurements laparoscopically. The device can be a unitary design, wherein a laparoscopic element includes electronics for the oximeter sensor at a distal end (e.g., opposite the tip). The device can be a multiple piece design (e.g., two-piece design), where some electronics is in a separate housing from the laparoscopic element, and the pieces (or portions) are removably connected together. The laparoscopic element can be removed and disposed of; so, the electronics can be reused multiple times with replacement laparoscopic elements. The electronics can include a processing unit for control, computation, or display, or any combination of these. However, in an implementation, the electronics can connect wirelessly to other electronics (e.g., another processing unit) for further control, computation, or display, or any combination of these.

In an implementation, an oximeter probe utilizes a sensor head positioned at a tip of an attached laparoscopic element to make oximetry measurements of a patient's internal tissue that is under investigation. The probe can use sensor head position on the laparoscopic element in combination with a relatively large number of simulated reflectance curves to quickly determine the optical properties of such internal tissue under investigation. The optical properties of the tissue allow for the further determination of the oxygenated hemoglobin and deoxygenated hemoglobin concentrations of the tissue as well as the oxygen saturation of the tissue.

In an implementation, an oximeter probe has a handpiece and a laparoscopic element connected to the handpiece. The handpiece and the laparoscopic can be releasably connected or not releasably connected. The releasable connection and nonreleasable connections of the handpiece and laparoscopic element facilitate reuse of the handpiece and disposal of the laparoscopic element or reuse of the handpiece, which houses a number of relatively costly electrical components, and disposal of the laparoscopic element after use. The oximeter probe includes a number of electrical components, including a transmitter that facilitates the transmission of oximeter information generated by the probe to a display. The display then displays one or more pieces of oximeter information transmitted from the oximeter probe. The display can be a display included in a laparoscopic tower used for laparoscopic surgery.

In an implementation, an oximeter probe has a handpiece and a laparoscopic element connected to the handpiece. The handpiece and the laparoscopic can be releasably connected or nonreleasably connected. The releasable connection and nonreleasable connections of the handpiece and laparoscopic element facilitate reuse of the handpiece and disposal of the laparoscopic element or reuse of the handpiece, which houses a number of relatively costly electrical components, and disposal of the laparoscopic element after use. The oximeter probe includes a number of electrical components, including a transmitter that facilitates the transmission of oximeter information generated by the probe to a display. The display then displays one or more pieces of oximeter information transmitted from the oximeter probe. The display can be a display included in a laparoscopic tower used for laparoscopic surgery.

In another implementation, an oximeter probe has a first portion and second portion that are rigidly fixed with respect to each other. The first portion has an elongated laparoscopic element. The laparoscopic element extends in a first direction and includes a proximal end and a distal end, opposite the proximal end. The element has a smooth outer surface and an interior tubular space. The interior tubular space has a first cross-section transverse to the first direction, and the first cross-section includes a first length.

The probe includes a sensor head that is connected to the distal end of the laparoscopic element. The interior tubular space of the laparoscopic element extends from a first opening at the proximal end of the laparoscopic element to the sensor head. The sensor head has a first structure and second structure, the first structure is an emitter, and the second structure is a detector.

The second portion is connected to the first portion at the distal end. The second portion has a first enclosure having a second cross-section transverse to the first direction, and the second cross-section includes a second length that is larger than the first length.

The first enclosure has an analog-to-digital converter circuit, connected to the second structure of the sensor head. The first enclosure also has an interface circuit, connected to the analog-to-digital converter circuit. The first enclosure also has a battery that is connected to the analog-to-digital converter and interface circuit.

In an implementation, the oximeter probe is a tissue oximeter and can measure oxygen saturation without needing a pulse or heart beat. An oximeter probe is applicable to many areas of medicine and surgery including abdominal surgery, plastic surgery, breast reconstruction, and other surgeries. The oximeter probe can make oxygen saturation measurements of tissue where there is no pulse and where there is a pulse. In an implementation, the oximeter probe is a pulse oximeter. In contrast to a tissue oximeter probe, a pulse oximeter uses a pulse in order to make measurements. A pulse oximeter typically measures the absorption of light due to the pulsing arterial blood.

In an implementation, a method includes providing an oximeter probe having a sensor head with a first structure and a second structure, the first structure is an emitter, and the second structure is a detector, and the oximeter probe includes a first wireless transceiver. The oximeter probe is connected to a system unit. The system unit includes a second wireless transceiver and a processing unit, where the second wireless transceiver communicates wirelessly with the first wireless transceiver of the oximeter probe through a direct wireless connection (e.g., point-to-point wireless). Using the detector, light is received and converted into electrical signal information. The electrical signal information on the received light is converted into digital signal information. Using the first wireless transceiver, the digital signal information is transmitted over the direct wireless connection.

The method can further include using the second wireless transceiver, receiving the digital signal information from the oximeter probe. The digital signal information is processed using a processing circuit of the system unit to obtain an oxygen saturation value. The oxygen saturation value is displayed on a display (e.g., LCD or OLED panel) of the system unit.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 6 shows a block diagram of an oximetry system that includes an oximeter probe and a display in an implementation.

FIG. 13 shows a block diagram of an oximetry system that includes an oximeter probe and a display in an implementation.

FIG. 17 shows a block diagram of an oximetry system that includes an oximeter probe and a display in an implementation.

DETAILED DESCRIPTION OF THE INVENTION

Figure 1:
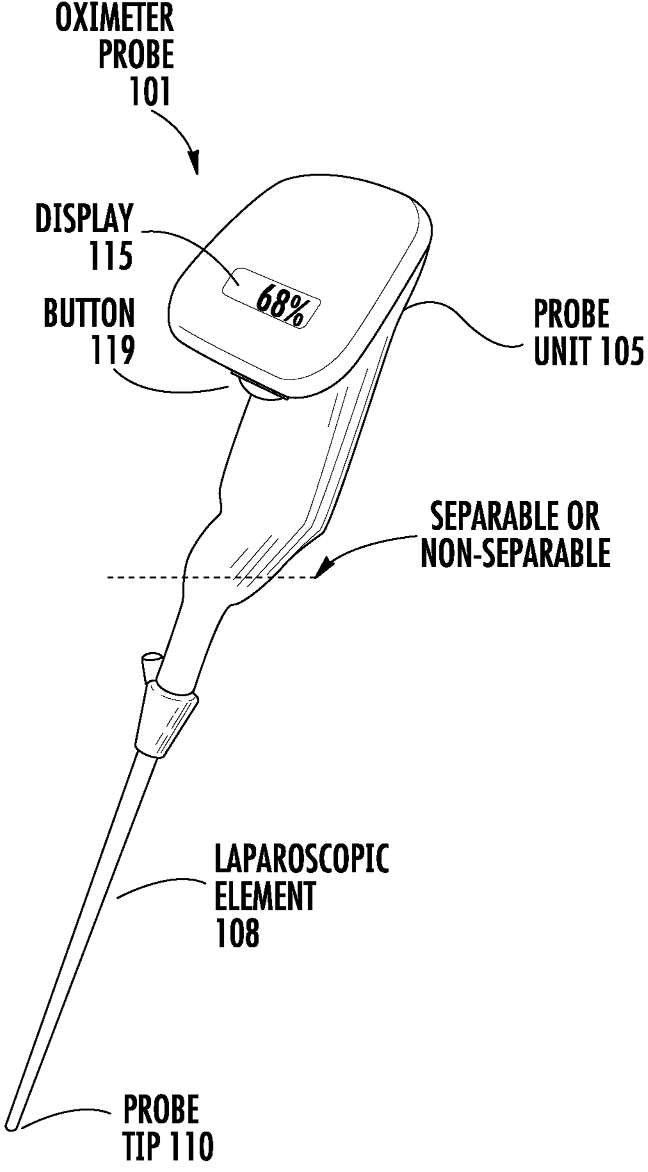
FIG. 1 shows an image of an oximeter probe having a laparoscopic element in an implementation.

FIG. 1 shows an image of an oximeter probe 101 in an implementation. Oximeter probe 101 is configured to make tissue oximetry measurements of tissue, such as internal tissue, intraoperatively. Oximeter probe 101 may be a handheld device that includes a probe unit 105 and a laparoscopic element 108 extending from the probe unit. A sensor head is positioned at a tip 110 of the laparoscopic element. The oximeter probe can include one or more user-input devices, such as one or more buttons 119. In some implementations, the display is a user-input device and includes a touch pad.

Oximeter probe 101 is configured to measure the oxygen saturation of internal tissue intraoperatively by positioning the laparoscopic element in a patient's body cavity and by emitting light, such as near-infrared light, from probe tip 110 into the tissue. Thereafter, the light reflected from the internal tissue is collected by the probe tip for determining the oxygen saturation of the tissue. Oximeter probe 101 includes a display 115 or other notification device that notifies a user of the oxygen saturation information for oximeter measurements made by the oximeter probe.

Oximeter probe 101 is a handheld device that can be held in the hand of medical provider for use. The probe unit is adapted to be held while the laparoscopic element is positioned in a patient's body cavity. The patient can be a human patient or animal patient in a veterinary medical environment. The probe unit and the laparoscopic element can be separable or not separable. In an implementation were the probe unit and the laparoscopic element are not separable, the oximeter probe may be a disposable device. Alternatively, where the probe unit and the laparoscopic element are separable, the probe unit may be reusable and the laparoscopic element may be disposable or the laparoscopic element might be adapted to be sterilized for subsequent reuse.

The laparoscopic element can be removably connected to the probe unit by one or more connector devices. For example, the laparoscopic element can include a twist lock device that is adapted to twist lock the laparoscopic element to the probe unit. Alternatively, the laparoscopic element can be pressed into contact with the probe unit and latched into place via a latch, a setscrew, a rotatable collar that pulls the laparoscopic element into contact with the probe unit, or other device. The laparoscopic element and probe unit can include one or more registration elements (e.g., slots and grooves) that facilitate registration and connection of electrical connectors and registration and connecting of light guides (e.g., sometimes referred to as waveguides), such as optical fibers, or both.

Figure 2:
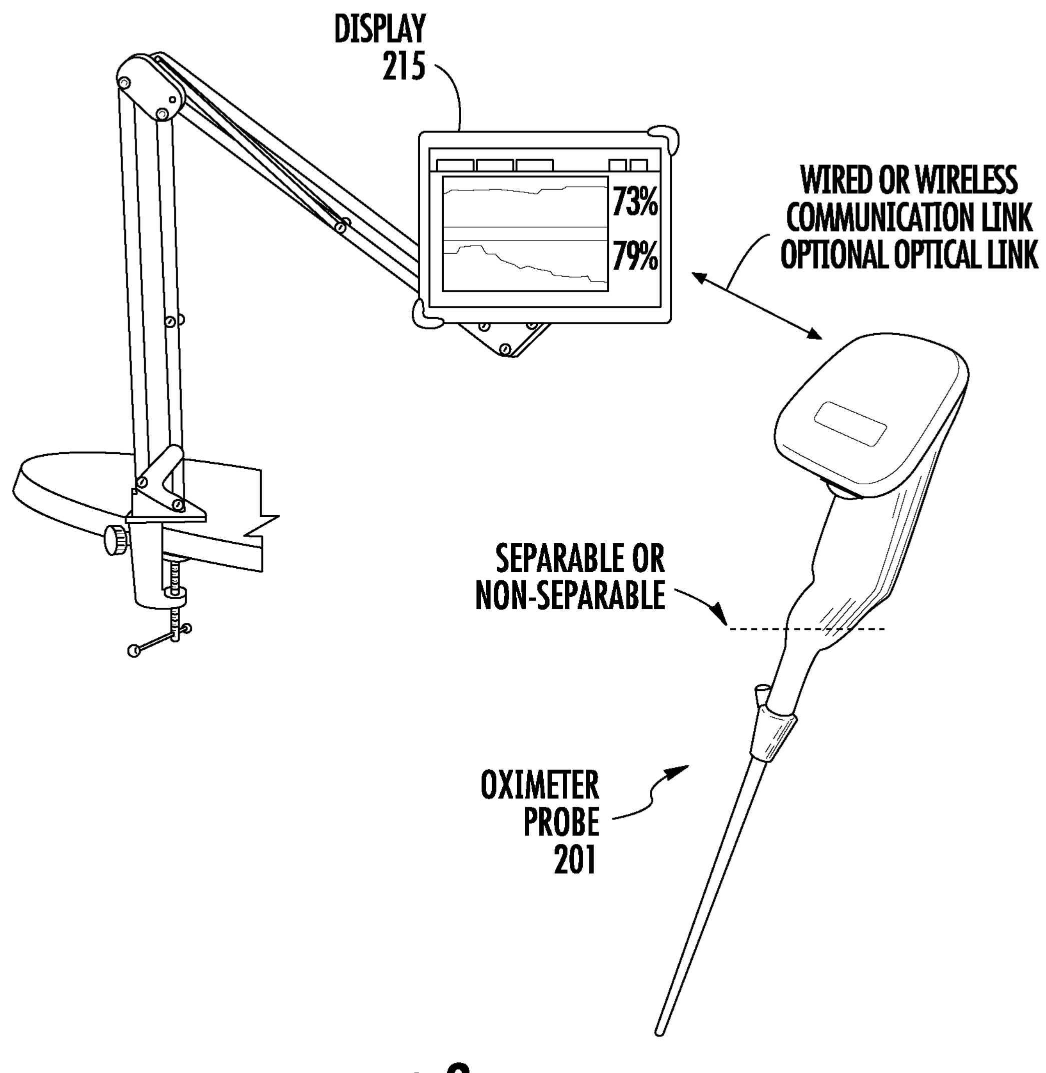
FIG. 2 shows an oximeter probe where the probe is adapted to communicate with a remote display.

FIG. 2 shows an oximeter probe 201 that is adapted to communicate with a display 215 (sometimes referred to as a system unit). Oximeter probe 201 can be similar to oximeter probe 101 described above where the laparoscopic element can be separable or not separable from the probe unit. The oximeter probe may be disposable if the probe unit and laparoscopic element are not separable, or the probe unit may be reusable and the laparoscopic element may be disposable if the probe unit and laparoscopic element are separable. Alternatively, the laparoscopic element can be adapted to be sterilized (e.g., by autoclaving) for reuse with the probe unit from which the laparoscopic element was detached or with a different probe unit.

Display 215 is adapted to display information for oxygen saturation measurements generated by the oximeter probe and transmitted to the display from the probe. Oximeter probe 201 and display 215 may be adapted to communicate via wired (e.g., cable) communication or wireless communication. The communication link can operate according to one of a variety of protocols, such as one of the Bluetooth protocols (e.g., Bluetooth, Bluetooth SMART, Bluetooth Low Energy, others), one of the IEEE 802.11 protocols, ANT, 6LoWPAN, MyriaNed, EnOcean, Z-Wave, Wi-Fi, one of the IEEE 802.15.4 protocol, such as ZigBee, or others. These or other wireless protocols can be used by the device to transfer data from the device to the display at 0.5 kilohertz to 500 kilohertz, such as approximately 250 kilohertz. Data transfer from the display to the device can be at similar rates.

The wireless link between the oximeter probe and the display is a direct wireless connection in an implementation. That is, no intermediary transmitter circuits, receiver circuits, or transceiver circuits receive the wireless signal transmitted from the oximeter probe for subsequent for retransmission of the wireless signal to the display. Similarly, no intermediary transmitter circuits, receiver circuits, or transceiver circuits receive the wireless signal transmitted from the display for subsequent for retransmission of the wireless signal to the oximeter probe.

In an implementation where the oximeter probe is adapted to communicate with display 215 for the display of information for oxygen saturation measurements, the probe may not include a display, such as display 115. In this implementation, display 215 operates as the display for the probe. Alternatively, the oximeter probe may include display 115 and may be adapted to communicate with display 215 where the two displays may display the same, different, or complementary oximetry information.

Display 215 can be a tablet computer or other display type, such as a display that is included in a laparoscopic tower used with other laparoscopic devices used during a laparoscopic surgery. In an implementation where the display is a tablet computer, the display can be attached to a laparoscopic tower that might include other displays and other medical devices. The display can operate an Android mobile operating system or other operating system adapted for use with mobile devices.

Display 215 can store and operate one or more computer applications adapted for receiving information for oximeter measurements generated by the oximeter probe. The display, via the application, can process the information and display the information or a derivative of the information. For example, the oximeter probe can transmit information (e.g., a value) for blood oxygen saturation (StO2), the percentage of oxygenated hemoglobin (HbO2), the percentage of deoxygenated hemoglobin (Hb), the blood volume, the melanin concentration, or other oximetry information. The display can display one or more pieces of information for these values, such as the values themselves or derivatives of the values.

Alternatively, the oximeter probe can transmit substantially raw measurement data in digital or analog form to the display. Substantially raw measurement data includes data that has not been processed by the processor or any preprocessors. The substantially raw measurement data can be analog detector responses generated by the detectors that may or may not be conditioned, amplified, or both. The substantially raw measurement data can be digitized detector responses that are digitized by the oximeter probe via an analog-to-digital convertor housed within the oximeter probe. The display, via use of the application, can perform data processing on the raw measurement data to generate final measurement information for the tissue, such as a value for blood oxygen saturation (StO2), a value for the percentage of oxygenated hemoglobin (HbO2), a value for the percentage of deoxygenated hemoglobin (Hb), blood volume, melanin concentration, or other value. The display, via the application, can display one or more pieces of the oximetry information.

Alternatively, the oximeter probe can transmit partially processed measurement data to the display. Partially processed data can include data for which one or more calibration corrections have been made for intensity difference of light emitted by the LEDs, inherent sensitivity differences of the photodetectors, or both. The display, via use of the application, can perform data processing on the partially processed data to generate final measurement information for the tissue, such as a value for blood oxygen saturation (StO2), a value for the percentage of oxygenated hemoglobin (HbO2), a value for the percentage of deoxygenated hemoglobin (Hb), blood volume, melanin concentration, or other value. The display, via the application, can display one or more pieces of the oximetry information.

The following U.S. patent applications are incorporated by reference along with all other references cited in this application: Ser. Nos. 13/887,130, 13/887,220, 13/887,213, 13/887,178, and 13/887,152, filed May 3, 2013; Ser. No. 13/965,156, filed Aug. 26, 2013; Ser. No. 15/493,132, 15/493,111, 15/493,121, filed Apr. 20, 2017; Ser. No. 15/494,444, filed Apr. 21, 2017; and Ser. No. 15/495,194, 15/495,205, and 15/495,212, filed Apr. 24, 2017. The above applications describe various oximeter devices and oximetry operations, and discussion in the above applications can be combined with aspects of the invention described in this application, in any combination.

Figure 3:
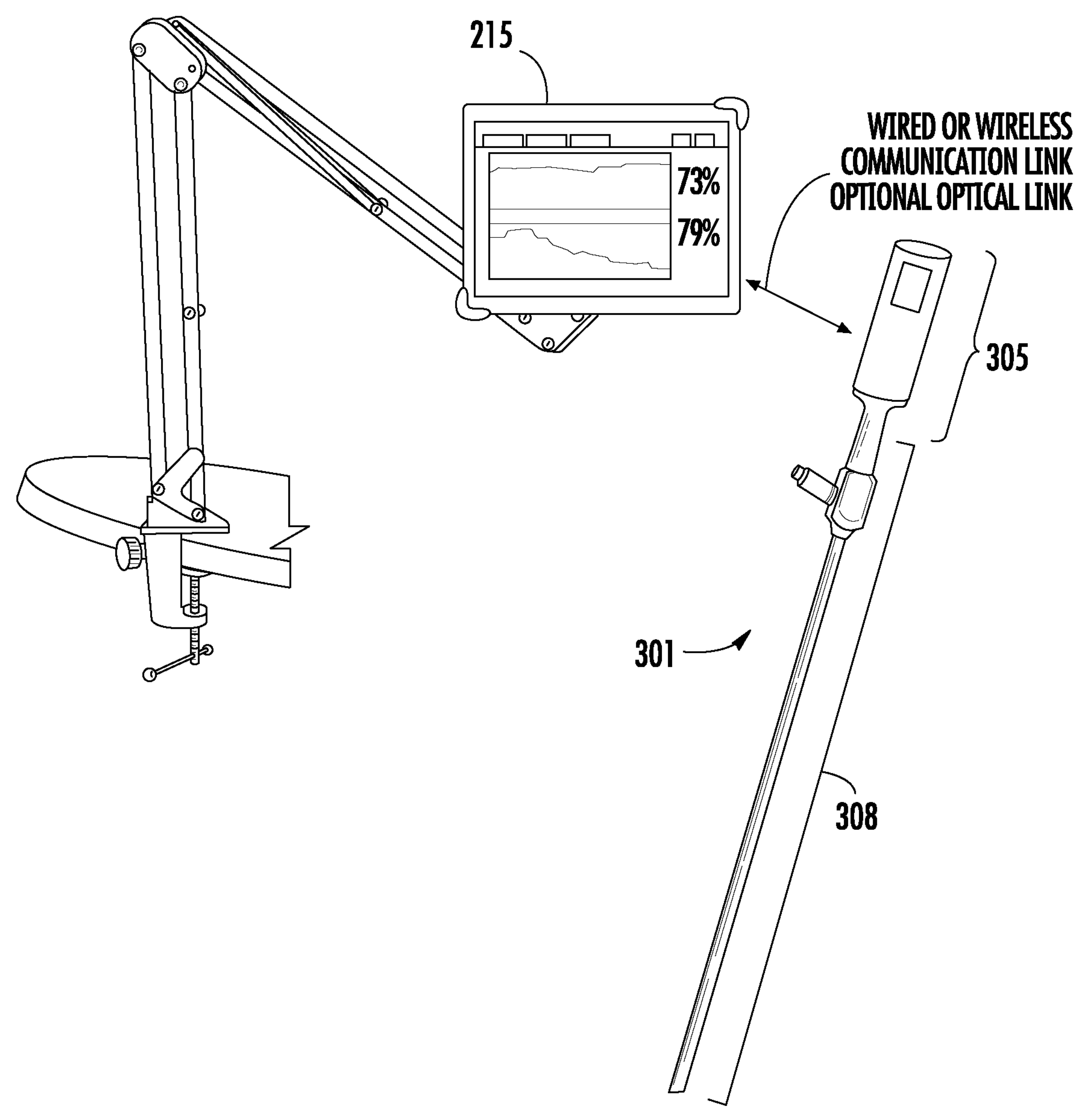
FIG. 3 shows an oximeter probe having a different form factor compared to probes shown in FIGS. 2 and 3.

FIG. 3 shows an oximeter probe 301 having a probe unit 305 and a laparoscopic element 308. The oximeter probe has a different form factor compared to probes 101 and 201. The oximeter probes described herein can have a variety of form factors other than the form factors shown in FIGS. 1-3.

Probe unit 305 (sometimes referred to as a reusable handpiece or simply a handpiece) is located at a top portion of the oximeter probe and may have a variety of shapes, such as rod shaped. The probe unit and the laparoscopic element may be separable or not separable, and the oximeter probe may be adapted for wire or wireless communication with the display 215.

Figure 4:
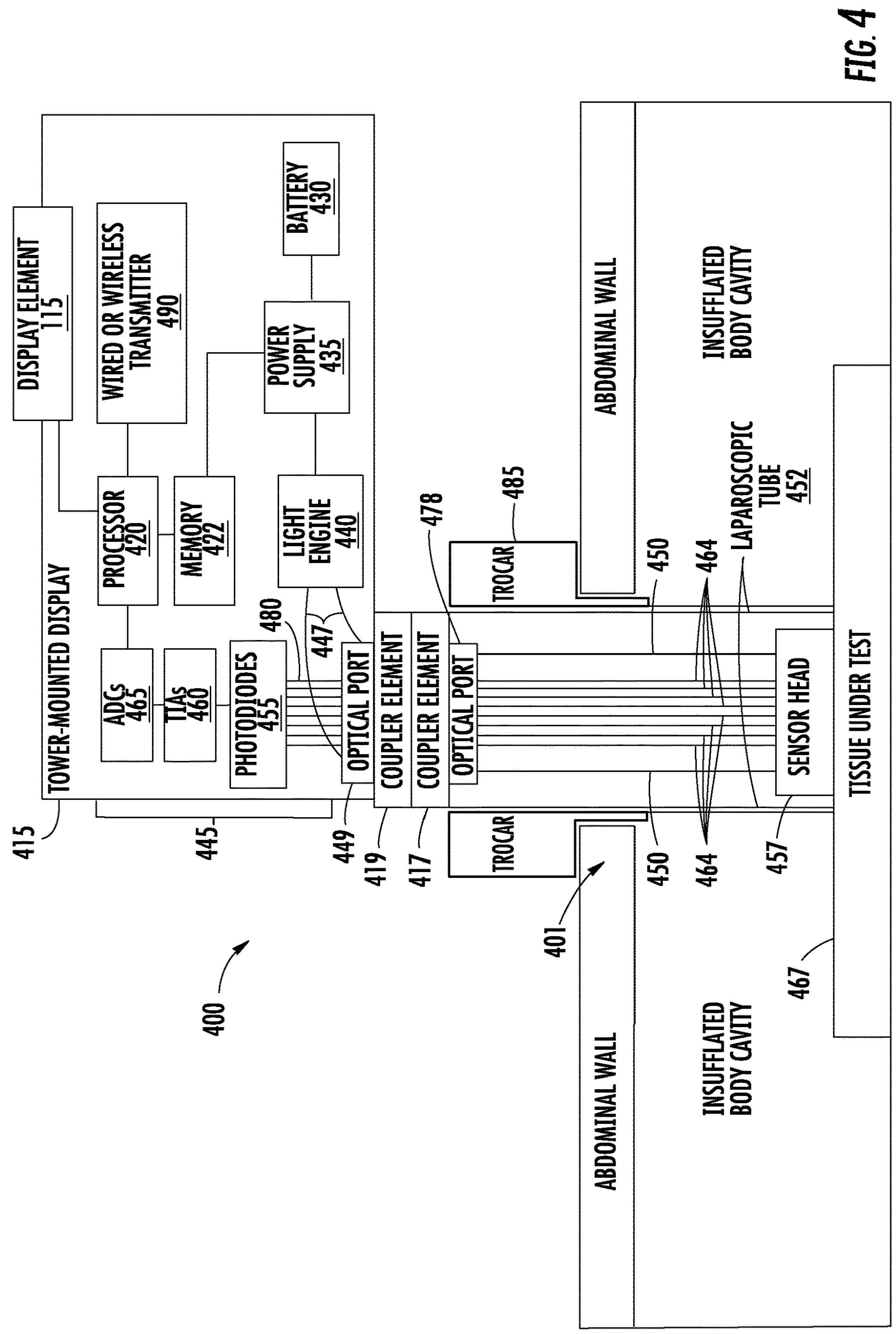
FIG. 4 shows a block diagram of an oximetry system that includes an oximeter probe and a display in an implementation.

FIG. 4 shows a block diagram of an oximetry system 400 that includes an oximeter probe 401 and a display 415 in an implementation. The oximetry system is adapted to determine one or more pieces of oximetry information regarding patient tissue 467, such as a value for absolute StO2, relative StO2, total hemoglobin, blood volume, melanin concentration, or other tissue information. The oximeter probe is adapted to emit light into the tissue and collect light reflected from the tissue to determine the oximetry information.

Display 415 includes a processor 420, a memory 422 electrically connected to the processor, a display element 115 electrically connected to the processor, a battery 430, and a power supply unit 435 that is adapted to supply power from the battery to the electrical components of the display. Electrical circuitry of the oximetry system performs the processing of signal data, controls operation of the system, performs calculations, determines oxygen saturation and other oximeter measurements, and other processing operations. This electronic circuitry may be referred to as a processing circuit and can include one or more electrical components or circuits, such as a processor, microprocessor, microcontroller, application specific integrated circuit (ASIC), field programmable gate array (FPGA), gate array, multiplexers, standard cells, control logic (e.g., programmable logic, programmable logic device (PLD), CPLD, and others), memory, look-up tables, state machines, logic gates, digital signal processors (DSP), and others. In an implementation, the processing circuit performs operations in digital (e.g., Boolean logic). But in other implementation, the processing circuit can be analog.

Some implementations of the display include a transceiver 490 (wired, wireless, or both) that is electrically connected to the display. In some implementations, the transceiver is a wired or wireless transmitter or a wired or wireless receiver. The display includes a light engine 440 and a detector stack 445. Different implementations of display 415 may include any number of the listed components, in any combination or configuration, and may also include other components not shown. The display includes coupler element 419 and an optical port 449.

Processor 420 can include one or more of a microprocessor, a microcontroller, a multi-core processor, or other processor type. Memory 422 may include one or more of a variety of memories, such as a volatile memory (e.g., a RAM), a nonvolatile memory (e.g., a disk or FLASH), or other memory types.

Battery 430 can include one or more of a variety of battery types, such as one or more disposable batteries or one or more rechargeable batteries. Disposable batteries are discarded after their stored charge is expended. Some disposable battery chemistry technologies include alkaline, zinc carbon, or silver oxide. The battery has sufficient stored charge to allow use of the handheld device for several hours. In an implementation, the oximeter probe is a disposable.

In implementations where the battery is rechargeable, the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the display can include a recharger circuit (not shown).

The light engine is electrically connected to the processor and the processor controls generation of light by the light engine for emission of the light into tissue 467. The light engine includes one or more sources that generate and transmit light, such as visible light, infrared light, or both. Each source can include one or more light emitting diodes (LEDs), such as one, two, three, four, five, six, seven, eight, nine, ten, or more LEDs. Each LED is adapted to emit one or more wavelengths of light, such as visible light, infrared light, or both. The LEDs can be discrete LEDs, organic LEDs (OLEDs), high brightness LEDs (HLEDs), quantum dot LEDs, laser diodes, or other types of LEDs.

The LEDs are optically connected to first ends of one or more source light guides 447, which are housed in the display. The light guides can be optical fibers or other light guiding elements. One, two, three, four, five, or more LEDs can be optically connected to one light guide 447. Second ends of the light guides are optically connected to a first optical port 449 of the display.

Detector stack 445 includes one or more of photodetectors 455, such as PIN photodiodes, phototransistors, photoresistors, or other detector type. The detector stack also includes one or more transimpedance amplifiers (TIAs) 460. The photodetectors convert received light into electrical signals, which the TIAs amplify. Each photodetector may be electrically connected to one TIA. In an implementation, multiple photodetectors are connected to a single TIA, for example, via a multiplexer. The TIAs are adapted to receive analog detector responses generated by the photodetectors. The TIAs convert the current for the analog detector responses to a voltage and amplify the voltage.

In some implementations, the display includes one or more electrical components that perform these functions, such as one or more current to voltage converters and one or more voltage amplifiers. It will be understood that a TIA is one example of an electronic circuit that can perform the conversion and amplification.

The photodetectors may generate output current (e.g., detector responses) that changes relatively linearly with the changing intensity of detected light, whereas the generated output voltage changes relatively nonlinearly with the changing intensity of detected light. The TIA or current to voltage converter can output relatively linear voltage from the current to voltage conversion. Thereafter, the amplified voltage is also relatively linear.

The detector stack includes one or more analog-to-digital converters (ADCs) 465. Each TIA may be electrically connected to one ADC. In an implementation, multiple TIAs are connected to one ADC, for example, via a multiplexer. The ADCs are also electrically connected to the processor. The ADCs digitize the amplified voltage signal received from the TIAs and transfer the digitized detector responses to the processor.

The ADC is samples the analog signal at a sampling rate. For example, the sampling rate can be about 0.33 hertz, about 1 hertz, about 2 hertz, about 3 hertz, or about 1-3 hertz (depending on conditions). In other implementations, the rate can be above 3 hertz, such as from about 4 hertz to about 1 kilohertz. Generally, the faster the sampling rate, the more power than is consumed which is a consideration for a battery-operated device, and also the data generated increase with sample rate. When using a sample rate of from about 0.33 to about 3 hertz, the amount of data can be transmitted wireless using technologies such as Bluetooth and Wi-Fi (and others mentioned in this patent) without data loss. In other implementations, a proprietary wireless technology can be used, such as when higher samplings rates are desired.

The detector stack can include one or more detector light guides 480. The light guides can be optical fibers or other light guiding elements. In an implementation, each photodetector is optically connected to a first end of one of the light guides and receives light transmitted through the light guide. Second ends of the light guides are connected to the optical port of the display.

The oximeter probe can be configured as a laparoscopic element that includes a laparoscopic tube 452, a coupler 417 that may be positioned at a first end of the laparoscopic element, and a sensor head 457 positioned at a second end of the laparoscopic element.

The laparoscopic element includes light guides 450 that are sometimes referred to as source light guides, and includes light guides 464 that are sometimes referred to as detector light guides. The light guides can be optical fibers or other light guiding elements. First ends of light guides 450 and 464 are optically connected to an optical port 478 of the laparoscopic element. Second ends of the light guides 450 and 464 extend through the laparoscopic element to sensor head 457. The optical port is distally positioned on the laparoscopic element relative to the sensor head.

Turning to coupler elements 417 and 419, the coupler elements are adapted to releasably connect to each other and in-turn releasably connect the oximeter probe to the display. Couplers 417 and 419 can mechanically couple the probe and display, can optically connect the probe and the display, can electrically connect the probe to the display, or can facilitate one or more of these connections in any combination.

Specifically, the connections of couplers 417 and 419 facilitates optical connections of the first and second optical ports 449 and 478 and thereby facilitates optical connections of light guides 447 and 450, and light guides 464 and 480.

In an implementation, the oximeter probe or the display includes an optical cable that optically links display 415 to oximeter probe 401. Specifically, the optical cable optically links light guides 447 and 450, and light guides 464 and 480.

The optical cable can be releasably or nonreleasably connected to the display, can be releasably or not releasably connected to the oximeter probe, and can include coupler element 419 or 417 or other coupler elements.

The optical cable can have a variety of lengths, such as 0.5 meters, 1 meter, 1.5 meters, 2 meters, or longer. The optical cable can be relatively flexible allowing the oximeter probe to be relatively freely moved for surgery.

When couplers 417 and 419 are connected, light emitted from the LEDs is transmitted into light guides 447 and thereafter is transmitted through light guide 477 to light guides 450. Light transmitted through light guides 450 is transmitted to the sensor head and can thereafter be transmitted out from the sensor head into tissue 467.

Light collected by the sensor head is transmitted through light guides 464 to light guides 480. Light guides 480 transmit the light to photodetectors 455. The photodetectors generate analog detector responses that are amplified by the TIAs and transmitted from the TIAs to the ADCs. The ADCs digitize the analog detector response output from the TIAs and transmit the digitized detector responses for the collected light to the processor. The processor can determine a variety of information for the tissue under examination based on the detector responses, such as absolute StO2, relative StO2, total hemoglobin, blood volume, or other information. Oximetry information generated by the processor can be displayed on display element 115, stored in memory 422, or transmitted via a wired or wireless transceiver 490 to other electrical devices.

In an implementation, the laparoscopic element is adapted for intraoperative use in a patient and can be introduced into the abdominal cavity of a patient through a trocar 485. An outer surface of the laparoscopic element can be smooth so that the laparoscopic element can slide through the trocar smoothly, rotated within the trocar smoothly, and can slide into and past patient tissue smoothly and without abrading the tissue. The oximetry system can be used on various internal tissue to determine various oximetry information for the tissue. The tissue under test can include intestinal tissue, such as the large intestine, small intestine, tissue that supports these tissues such as the mesentery tissue, the liver, kidneys, or other tissue.

Figure 5:
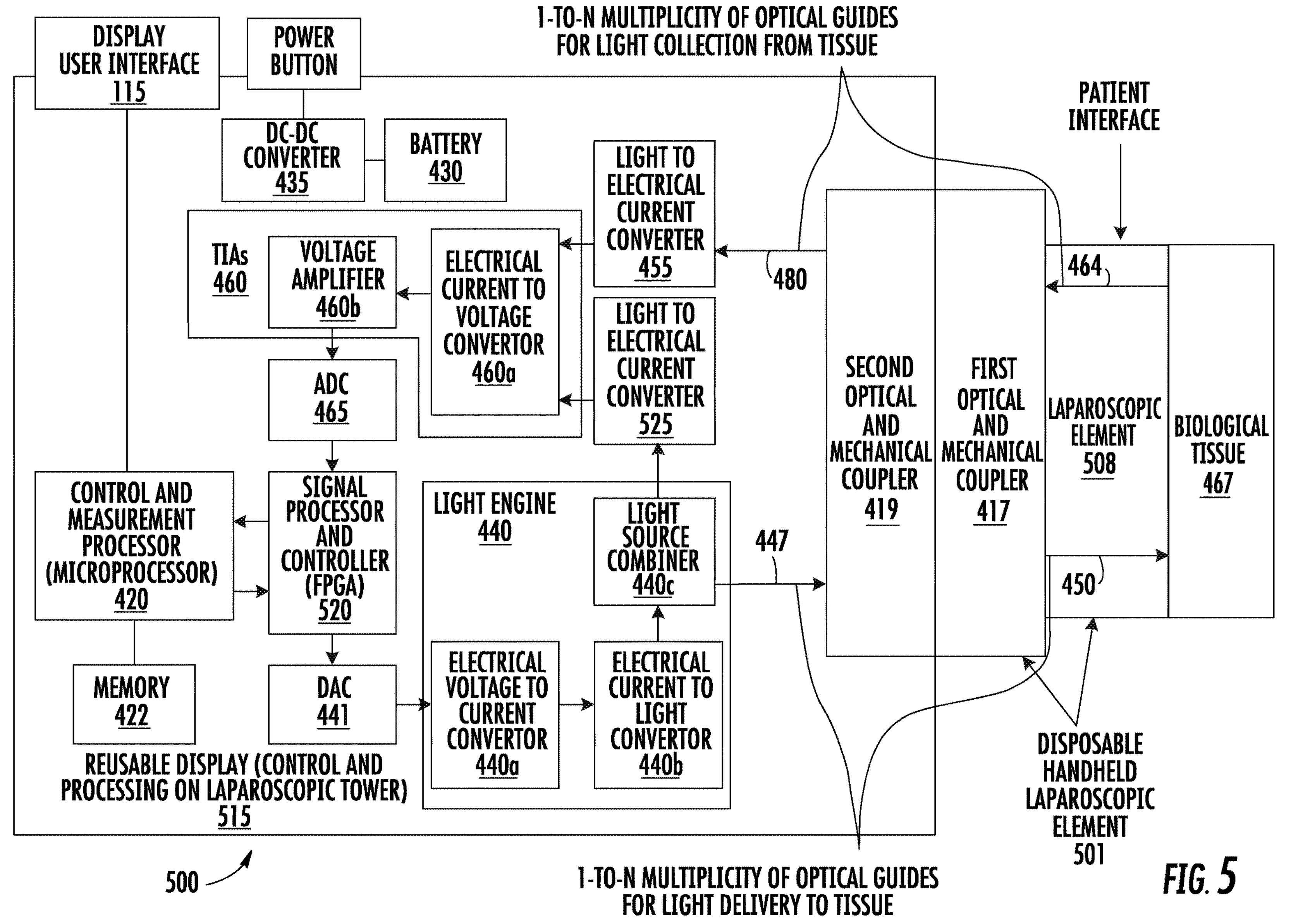
FIG. 5 shows an oximetry system in an implementation.

FIG. 5 shows an oximetry system 500 in an implementation. Oximetry system 500 includes an oximeter probe 501 and a display 515. Oximetry system 500 is similar to oximetry system 400 but differs in that display 515 of the oximetry system includes a signal acquisition processor 520 (sometimes referred to as a preprocessor) that is adapted to receive digitized information for oximetry measurements from the ADCs 465 and preprocess the digitized information for subsequent transmission and processing by processor 420.

The signal acquisition processor can include a field programmable gate array (FPGA) or a programmable logic device (PLD), such as a complex PLD (CPLD). In implementations where the display includes an FPGA or a CPLD, the FPGA or a CPLD can be adapted to perform preprocessing on collected information prior to transmitting the preprocessed information to the processor for further processing. The FPGA or CPLD can be electrically positioned between the ADCs and the processor.

Preprocessing can include applying one or more correlation calculations to digitized detector responses received from the ADCs, such as performing one or more calibration steps on the data. Calibration can include calibrating the digitized detector responses for inherent discrepancies of the intensity of light emitted by the LEDs, for inherent discrepancies of the detection sensitivity of the photodetectors, or both, or other correlation calculations. Calibration information for the LEDs and photodetectors 455 can be predetermined and stored in memory.

In an implementation, the display includes photodetectors 525, such as a PIN diodes, that are adapted to detect a portion of the light emitted by the LEDs of light engine 440 to determine whether the intensity of the emitted light by the LEDs increases or decreases during use of the oximetry system. The photodetectors may be electrically connected to the acquisition processor via one or more current to voltage converters 460*a* and amplifiers 460*b* (e.g., TIAs 460). Driver signals for the LEDs can be adjusted by acquisition processor 520, processor 420, or both to maintain relatively constant the intensity of the light that is output based on intensity information provided to the acquisition processor.

The light engine can include one or more electrical circuits, optical elements, or both. Specifically, the light engine can include a voltage to current convertor 440*a*, LEDs 440*b*, and a light combiner 440*c*. Convertor 440*a* can be connected to a digital to analog convertor (DAC) 441 that supplies control signals to the light engine from acquisition processor 520. The control signal output by converter 440*a* is supplied to LEDs 440*b* for light production. LEDs 440*b* can be optically connected to one or more optical fibers 447 in a one-to-one manner or the light from multiple LEDs can be combined onto a single optical fiber by a light source combiner 440*c*. Combiner 440*c* can include one or more lenses, reflective elements, optical combiners, or other optical devices.

The display may include one or more temperature measurement devices, e.g. thermistors (not shown) that are positioned adjacent to the LEDs of the light engine. The thermistors can be connected to the acquisition processor via one or more amplifiers (not shown). The thermistors are adapted to detect the temperature of the LEDs during use of the oximetry system and transmit signals for the temperature to the amplifiers, which transmit the amplified output from the thermistors to the acquisition processor. Driver signals for the LEDs can be adjusted by the acquisition processor, the processor, or both to maintain the intensity of the light that is output relatively constant based on temperature information provided to the acquisition processor.

FIG. 6 shows a block diagram of an oximetry system 600 that includes an oximeter probe 601 and a display 615 in an implementation. Oximeter system 600 differs from oximeter system 500 in that a number of the optical and electrical components that are adapted for determining the oximetry information for the system are housed in the oximeter probe rather than the display.

Oximeter probe 601 is adapted to determine one or more pieces of oximetry information regarding patient tissue 467, such as a value for absolute StO2, relative StO2, total hemoglobin, blood volume, melanin concentration, or other tissue information. The oximeter probe is adapted to transmit the oximetry information to the display 615 for display.

Oximeter probe 601 can have a form factor similar to oximeter probe 101, 201, 301, or have other form factors. The oximeter probe includes a probe unit 605 (sometimes referred to as a reusable handpiece or simply a handpiece) and a laparoscopic element 608. The laparoscopic element can be separable or not separable from the probe unit. In an implementation where the oximeter probe is an integrated device that is not separable, the oximeter probe can be a disposable unit that may be disposed of after use with a single patient. Where the oximeter probe and laparoscopic probe unit are separable, the oximeter probe can be reusable and the laparoscopic element can be a disposable unit that may be disposed of after use with a single patient. Alternatively, the laparoscopic element can be adapted to be sterilized and reused with the probe unit or a different probe unit.

Probe unit 605 includes processor 420, memory 422 electrically connected to the processor, a transceiver 490 (e.g., wired or wireless) electrically connected to the processor, battery 430, and power supply unit 435. Each transmitter and receiver described in this patent can be a transceiver. The probe unit includes light engine 440 electrically connected to the processor, ADCs 465 electrically connected to the processor, and an analog wiring bundle 461. Different implementations of the probe unit may include any number of the listed components, in any combination or configuration, and may include other components not shown. The operation of these elements is described above with respect to FIG. 4.

Probe unit 605 includes coupler 419 and port 449. Coupler 419 can facilitate a mechanical connection, optical connection, and electrical connection with the laparoscopic element. Port 449 can be an optical port, an electrical port, or an optical and electrical port.

The probe unit, portions of the laparoscopic element, or both can be covered with a barrier 619. The barrier can inhibit fluids and debris from contacting portions of the oximeter probe that are covered by the barrier and isolates reusable and nonsterilizable portions of the oximeter probe from the sterile surgical field. The barrier is transparent to information displayed on a display of the oximeter probe in implementations where the probe includes a display, such as display 115. The barrier can be formed of plastic or plastic type materials that are flexible and can wrap around the covered portions of the oximeter probe. The barrier can be adapted to cover one or more portions of the oximeter probes described in this application.

Laparoscopic element 608 includes laparoscopic tube 452, coupler 417 that is positioned at a first end of the laparoscopic element, and a sensor head 657 that is positioned at a second end of the laparoscopic element. The laparoscopic element includes light guides 450. First ends of light guides 450 are optically connected to optical port 478 of the laparoscopic element. Second ends of the light guides 450 extend through the laparoscopic element to sensor head 657. The optical port is distally positioned on the laparoscopic element relative to the sensor head.

In addition to the sensor head, the laparoscopic element includes photodiodes 455, TIAs 460, and an analog wire bundle 462 (e.g., flexible cable). The sensor head 657 can include the photodiodes, the TIAs, or both. The TIAs are electrically connected between the photodiodes and the analog wire bundle. The sensor head, photodiodes, TIAs, and the wiring bundle are each positioned in the central opening (e.g., interior tubular opening) of the laparoscopic tube. The central opening can have a constant cross-section dimension (e.g., the cross-section is transverse to the longitudinal dimension of the laparoscopic element) from a top of the laparoscopic tube to the bottom of the laparoscopic tube (e.g., constant diameter for a round cross-section).

The connection of couplers 417 and 419 facilitates optical connection of the first and second optical ports 449 and 478 and thereby facilitates optical connection of light guides 447 and 450. The connection of couplers 417 and 419 also facilitate electrical connection of analog wire bundles 461 and 462. The connection of couplers 417 and 419 also facilitate the mechanical connection (e.g., fixed and rigid mechanical connection) of the probe unit to the laparoscopic element in an implementation.

The tip of the sensor head can be one of a variety of distances (e.g., the approximate length of the laparoscopic tube) from the top of the laparoscopic element based, for example, on the particular medical procedure that the oximeter probe is used for. For example, the distance can be 10 centimeters, 15 centimeters, 20 centimeters, 25 centimeters, 30 centimeters, 35 centimeters, 40 centimeters, 45 centimeters, 50 centimeters, 55 centimeters, or other lengths.

When the couplers are connected, light emitted from the LEDs is transmitted into light guides 447 and thereafter is transmitted through light guide 477 to light guides 450. Light transmitted through light guides 450 is transmitted to the sensor head and can thereafter be transmitted out from the sensor head into tissue 467. In an implementation where the probe unit and the laparoscopic element are nonseparable, light guides 450 and 477 are integrated as substantially continues light guides and wiring bundles 461 and 462 are integrated as a substantially continues wiring bundles.

Photodetectors 455 at the sensor head are adapted to detect the light subsequent to reflection from the tissue and generate detector responses (e.g., analog signals) from the detected light. The detector responses are transmitted from the detectors to the TIAs, which amplify the signals for the detector responses. The amplified detector responses are then transmitted to the ADCs in the probe unit via the analog wire bundles. The analog wire bundles can also be adapted to provide power and ground to the TIAs and the photodiodes. After receiving the digitized detector responses from the ADCs, the processor uses the detector responses to determine one or more pieces of oximetry information to the tissue, such as absolute StO2, relative StO2, total hemoglobin, blood volume, or other information.

Oximetry information generated by the processor can be displayed on a display 115 of the oximeter probe, can be transmitted by the transmitter to display 615 for display, can be stored in memory 422, or can be transmitted to other electrical devices. Display 615 can include a receiver (e.g., wired or wireless) 616 that receives the transmitted information from oximeter device. The display 615 includes a power source, such as a battery power source, that is a different battery source than the power source in the probe unit. The power source in the display 615 is electrically connected to the electronic unit in the display and powers the electronic units, such as the receiver, the display, and others.

Figure 7:
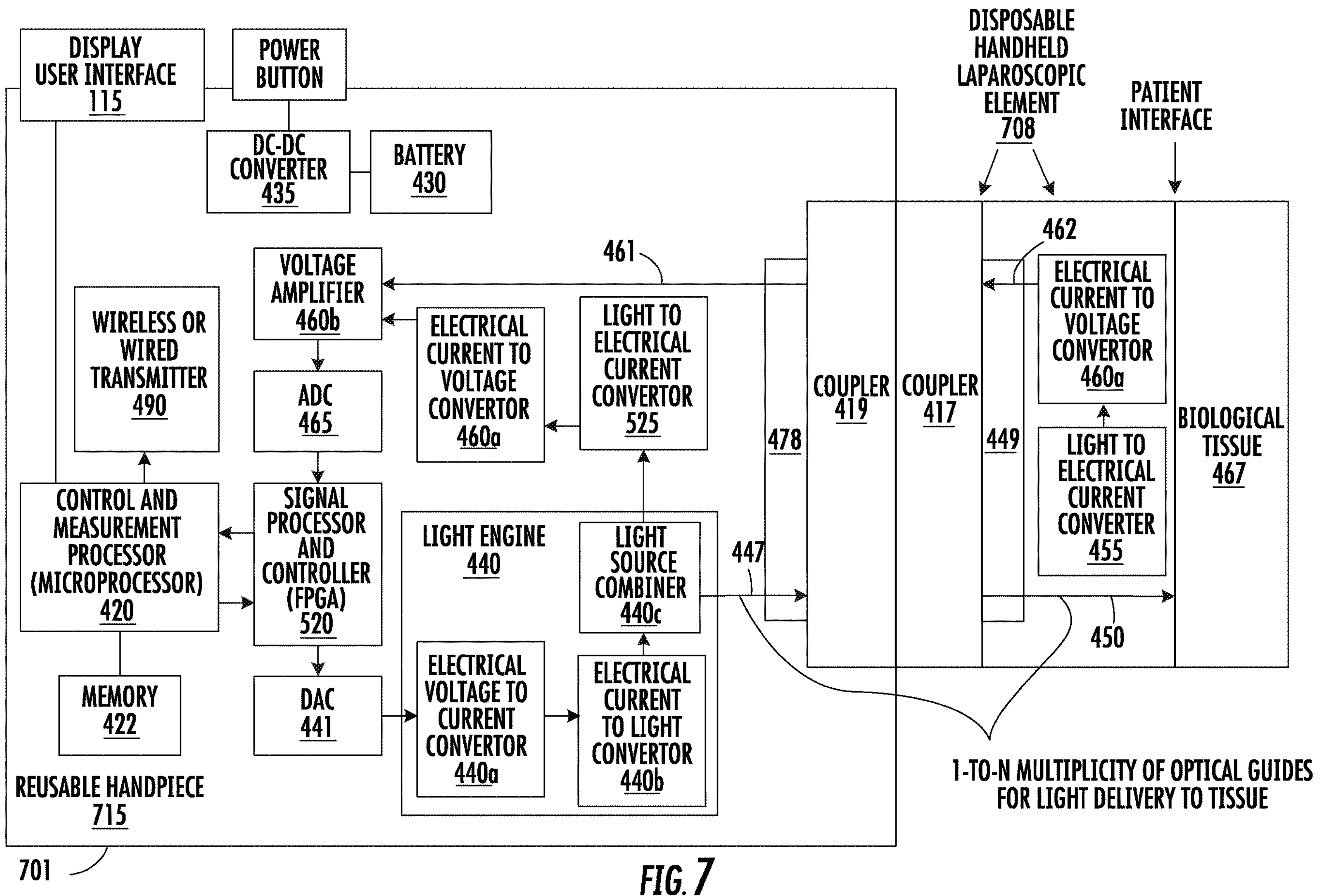
FIG. 7 shows an oximeter probe in an implementation.

FIG. 7 shows an oximeter probe 701 in an implementation. Oximeter probe 701 includes a probe unit 715 and a laparoscopic element 708. Probe unit 715 is adapted to communicate with a display, such as display 615 described above. Oximeter probe 701 is similar to oximeter probe 600 but differs in that probe unit 715 of the oximeter probe includes signal acquisition processor 520 that is adapted to receive digitized detector responses for oximetry measurements from ADCs 465 and preprocess the digitized detector responses for subsequent transfer to processor 420 for processing.

In an implementation, one or more current to voltage convertors **460*a* are housed in the laparoscopic element. The current to voltage converters are electrically connected to photodetectors 455 and are electrically connected to one or more voltage amplifiers 460*b*. The voltage amplifiers are housed in probe unit 715, but alternatively can be housed in laparoscopic element 708. The current to voltage converters and voltage amplifiers can be TIAs or other types of circuits. The current to voltage convertors and voltage amplifiers can be electrically connected via couplers 417 and 419**.

The probe unit may include one or more thermistors, such as those described above with respect to FIG. 5. The thermistors can be positioned physically adjacent to the LEDs of the light engine to monitor the temperature of the LEDs. The thermistors are electrically connected to the acquisition processor via one or more amplifiers. The thermistors are adapted to track the temperature of the LEDs during use of the oximetry system and transmit signals for the temperature to the amplifiers, which transmit the amplified signals to the acquisition processor. Using the amplified signals, the acquisition processor, the processor, or both can change the driver signals provided to the LEDs so that the generated light has a substantially constant intensity.

Probe unit 715 can include a display 115. Some implementations of the probe unit do not include a display. The display of probe unit 715 can display similar or different oximetry information than display 615 that may be attached to a laparoscopic tower. Display 115 is electrically connected to the processor or to the preprocessor, such as via an interface circuit (sometimes referred to as a transmitter) that is electrically positioned between the display and the processor or preprocessor.

Figure 8:
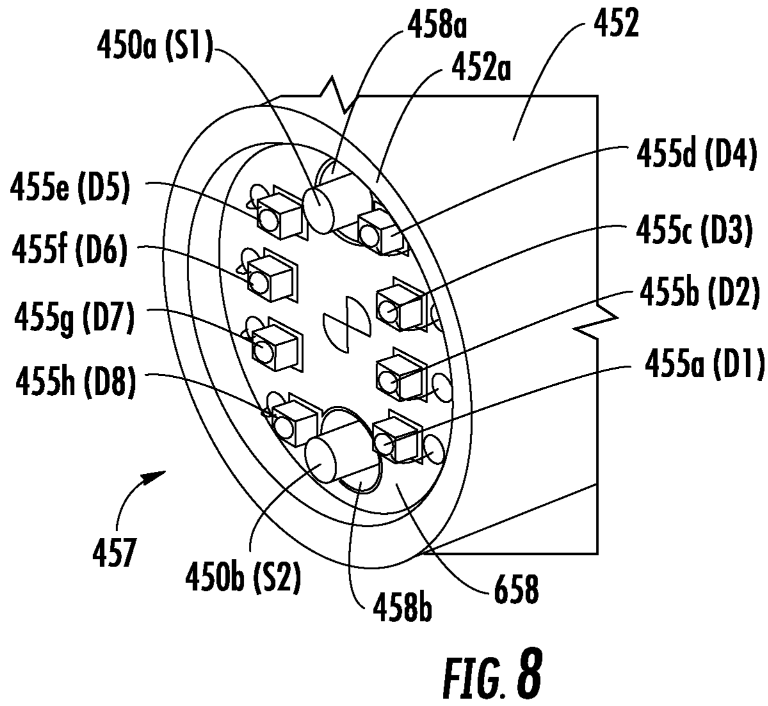
FIGS. 8 and 9 show a perspective view and an end view of a sensor head positioned in an end portion of a laparoscopic tube.
Figure 9:
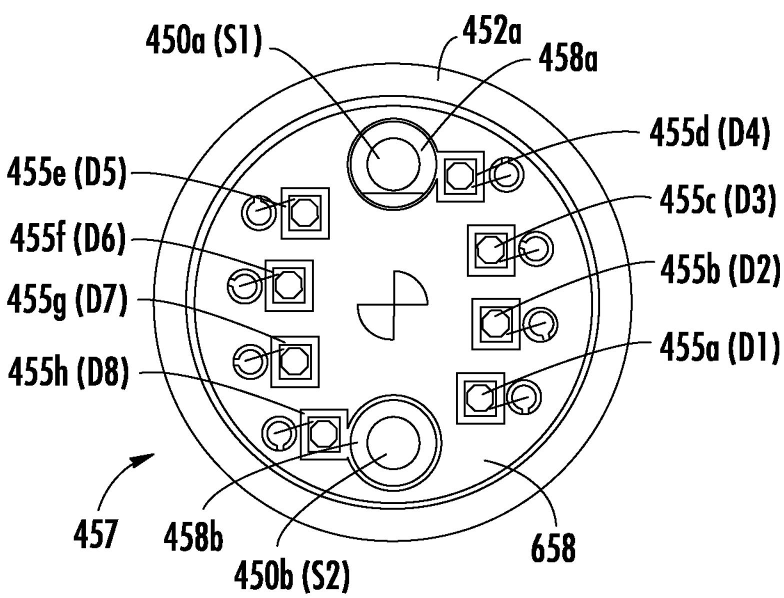

FIGS. 8 and 9 show a perspective view and an end view of sensor head 657 that is positioned in an end portion **452*a* of laparoscopic tube 452. The sensor head includes a printed circuit board (PCB) 658 that may be substantially round (e.g., circular) to fit in the end of the laparoscopic element. Detector structures (e.g., openings which light enters to reach waveguides or photodetectors, the tips of waveguides, or photodetectors) 544 (labeled 455*a*-455*h*) are positioned on the sensor head (e.g., on a surface of the PCB) that faces outward from an end opening of the laparoscopic tube. In the implementation shown in FIGS. 8 and 9, the detector structures are photodetectors. Two source structures (also sometimes referred to as emitters) from which light is emitted (e.g., cutouts, such as apertures, 458*a* and 458*b* are formed in the PCB) are formed in the sensor head. The source structures can be waveguides (e.g., the ends of optical fibers) or light sources (e.g., LEDs). End portions of light guides 450***a* and 450*b* are positioned in the apertures and extend through the apertures.

The photodetectors and ends of the light guides can be arranged in a variety of configurations. In an implementation, at least one source-to-detector distance is less than 1.5 centimeters and can be less than one centimeter, and at least two source-to-detector distances are greater than 2.5 centimeters. In another implementation, at least one source-to-detector distance is less than 1.5 millimeters and can be less than one millimeter, and at least one source-to-detector distance is greater than 2.5 millimeters or at least two source-to-detector distances are greater than 2.5 millimeters. In an implementation, the greatest source-to-detector distance is about 10 millimeters or less, about 5 millimeters or less, about 4.5 millimeters or less, about 4.1 millimeters or less, about 4 millimeters or less, or others.

In an implementation, the shortest source-to-detector distances (distances between the detectors and the ends of the light guides) are approximately equal. For example, the shortest source-to-detector distances are approximately equal between light guide 450*a* and photodetector 455*d* (S1-D4) and between light guide 450*b* and photodetector 455*a* (S2-D8) are approximately equal. The next longer source-to-detector distances (e.g., longer than each of S1-D4 and S2-D8) between light guide 450*a* and photodetector 455*e* (S1-D5) and between light guide 450*b* and photodetector 455*a* (S2-D1) are approximately equal. The next longer source-to-detector distances (e.g., longer than each of S1-D5 and S2-D1) between light guide 450*a* and photodetector 455*c* (S1-D3) and between light guide 450*b* and photodetector 455*g* (S2-D7) are approximately equal. The next longer source-to-detector distances (e.g., longer than each of S1-D3 and S2-D7) between light guide 450*a* and photodetector 455*f* (S1-D6) and between light guide 450*b* and photodetector 455*b* (S2-D2) are approximately equal. The next longer source-to-detector distances (e.g., longer than each of S1-D6 and S2-D2) between light guide 450*a* and photodetector 455*c* (S1-D2) and between light guide 450*b* and photodetector 455*f* (S2-D6) are approximately equal. The next longer source-to-detector distances (e.g., longer than each of S1-D2 and S2-D6) between light guide 450*a* and photodetector 455*g* (S1-D7) and between light guide 450*b* and photodetector 455*c* (S2-D3) are approximately equal. The next longer source-to-detector distances (e.g., longer than each of S1-D7 and S2-D3) between light guide 450*a* and photodetector 455*a* (S1-D1) and between light guide 450*b* and photodetector 455*e* (S2-D5) are approximately equal. The next longer source-to-detector distances (e.g., longest source-to-detector distance, longer than each of S1-D1 and S2-D5) between light guide 450*a* and photodetector 455*h* (S1-D8) and between light guide 450*b* and photodetector 455*d* (S2-D4) are approximately equal. In other implementations, the source-to-detector distances can all be unique or have fewer than eight distances that are approximately equal.

A table below shows the eight unique source-to-detector distances according to an implementation. The increase between nearest source-to-detector distances is approximately 0.4 millimeters.

TABLE

| Source-to-Detector Pairs | Source-to-Detector Distances Millimeters |
|---|---|
| (S1-D4) | 1.000 |
| (S2-D8) | 1.000 |
| (S1-D5) | 1.430 |
| (S2-D1) | 1.430 |
| (S1-D3) | 1.860 |
| (S2-D7) | 1.860 |
| (S1-D6) | 2.290 |
| (S2-D2) | 2.290 |
| (S1-S2) | 4.000 |
| (S1-S2) | 4.000 |
| (S1-D7) | 3.150 |
| (S2-D3) | 3.150 |
| (S1-D1) | 3.580 |
| (S2-D5) | 3.580 |
| (S1-D8) | 4.010 |
| (S2-D4) | 4.010 |

In an implementation, photodetectors 455*a* and 455*e* are symmetrically positioned about a point that is on a straight line connecting light guides 450*a* and 450*b*. Photodetectors 455*b* and 455*f* are symmetrically positioned about the point. Photodetectors 455*c* and 455*g* are symmetrically positioned about the point. Photodetectors 455*d* and 455*h* are symmetrically positioned about the point. The point can be centered between light guides 450*a* and 450*b* on the connecting line.

A plot of source-to-detector distance verses reflectance detected by photodetectors 455 can provide a reflectance curve where the data points are well spaced along the x-axis. These spacings of the distances between light guides 450*a* and 450*b*, and photodetectors 455 reduces data redundancy and can lead to the generation of relatively accurate reflectance curves.

In an implementation, the light guides and photodetectors can be arranged at various positions on the probe surface to give the distances desired (such as indicated above). For example, the two light guides form a line, and there will be equal number of photodetectors above and below this line. Additionally, the position of a photodetector (above the line) will have point symmetry with another photodetector (below the line) about a selected point on the line of the two light guides. As an example, the selected point may be the midpoint between the two light guides, but not necessarily. In other implements, the positioning can be arranged based on a shape, such as a circle, an ellipse, an ovoid, randomly, triangular, rectangular, square, or other shape, such as photodetectors 455*e*, 455*f*, 455*f*, and 455*h* arranged in a first arc and photodetectors 455*d*, 455*c*, 455*b*, and 455*a* arranged in a second arc. The first and second arcs can have the same or similar shapes when one of the arcs if vertically and horizontally flipped.

The oximeter device is adapted to use spatially resolved spectroscopy techniques for determining oximeter information, such as blood oxygen saturation, of tissue. Spatially resolved spectroscopy is facilitated by the source-to-detector spacing where at least one source-to-detector distance is less than 1.5 millimeters and can be less than one millimeter, and at least one source-to-detector distance is greater than 2.5 millimeters or at least two source-to-detector distances are greater than 2.5 millimeters. These source-to-detector distances can be achieved via a number or source and detector combinations, such as one source and two detectors, two sources and one detector, or other.

Spatially resolved spectroscopy is further facilitated by the memory storing and the processor using a number of simulated reflection curves, where each reflection curves represent an absorption coefficient and a scattering coefficient for the particular configuration of sources and detectors of the sensor head. One particular configuration of source-to-detector spacing are listed in table one and described in this patent, such as photodetectors 455*a* and 455*e* are symmetrically positioned about a point that is on a straight line connecting light guides 450*a* and 450*b*; photodetectors 455*b* and 455*f* are symmetrically positioned about the point; photodetectors 455*c* and 455*g* are symmetrically positioned about the point; and photodetectors 455*d* and 455*h* are symmetrically positioned about the point, where the point can be centered between light guides 450*a* and 450*b* on the connecting line.

The simulated reflection curves include reflection intensities (e.g., in arbitrary units) for light reflected from simulated tissue for a variety of wavelengths emitted from the oximeter device. The simulated reflectance curves can be of simulated tissue using a Monte Carlo simulation method.

The processor can determine one or more of the simulated reflectance curves that best fits (e.g., lowest fit error determined by a fit method, such as least squared or others) reflectance data generated by the detectors. The processor can them determine one or more absorption coefficients and one or more scattering coefficients for the tissue from the one or more simulated reflectance curves that best fits the reflectance data. From the absorption coefficient, the processor can then determine other oximeter information for measured tissue, such as oxygen saturation. The source-to-detector spacings of the sensor head (e.g., at least one source-to-detector distance is less than 1.5 millimeters and at least one source-to-detector distance is greater than 2.5 millimeters) facilitates that the absorption coefficient and the reduced scattering coefficient can be determined from the simulated reflectance curves where these coefficients are mathematically independent. Because the absorption coefficient and the reduced scattering coefficient are mathematically independence, further tissue measurements, further mathematical determinations, or both can be avoided, via the use of such spatially resolved spectroscopy.

Wavelengths emitted by each of the sources of the sensor head include two, three, four, or more different wavelengths of light (e.g., light includes infrared radiation). The emitted wavelength include 760 nanometers, 810 nanometers, 845 nanometers, and 895 nanometers in one implementation. Other wavelengths of light are emitted by the oximeter device including shorter and longer wavelengths of light in other implementations.

Figure 10:
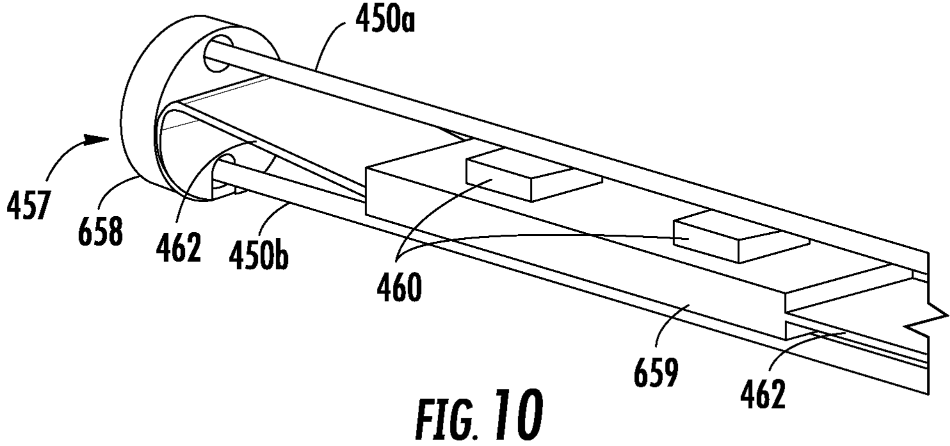
FIGS. 10, 11, and 12 show a first perspective view, a second perspective view, and a cross-sectional view of sensor head of an oximeter probe in an implementation.
Figure 11:
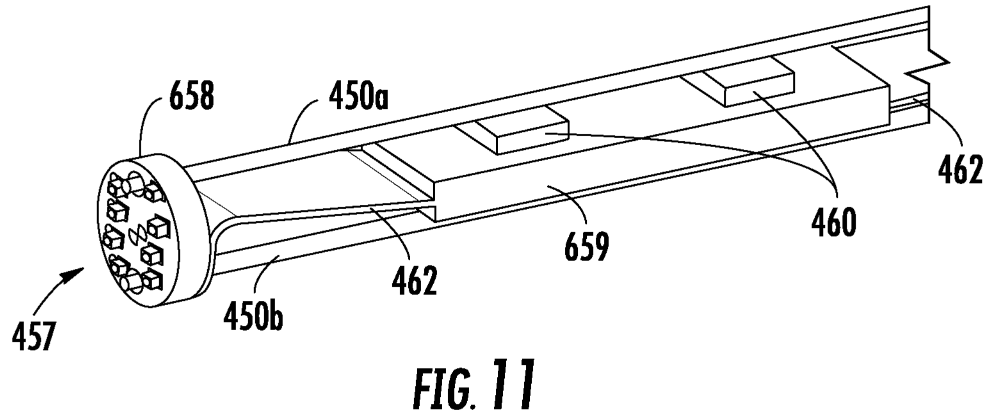
Figure 12:
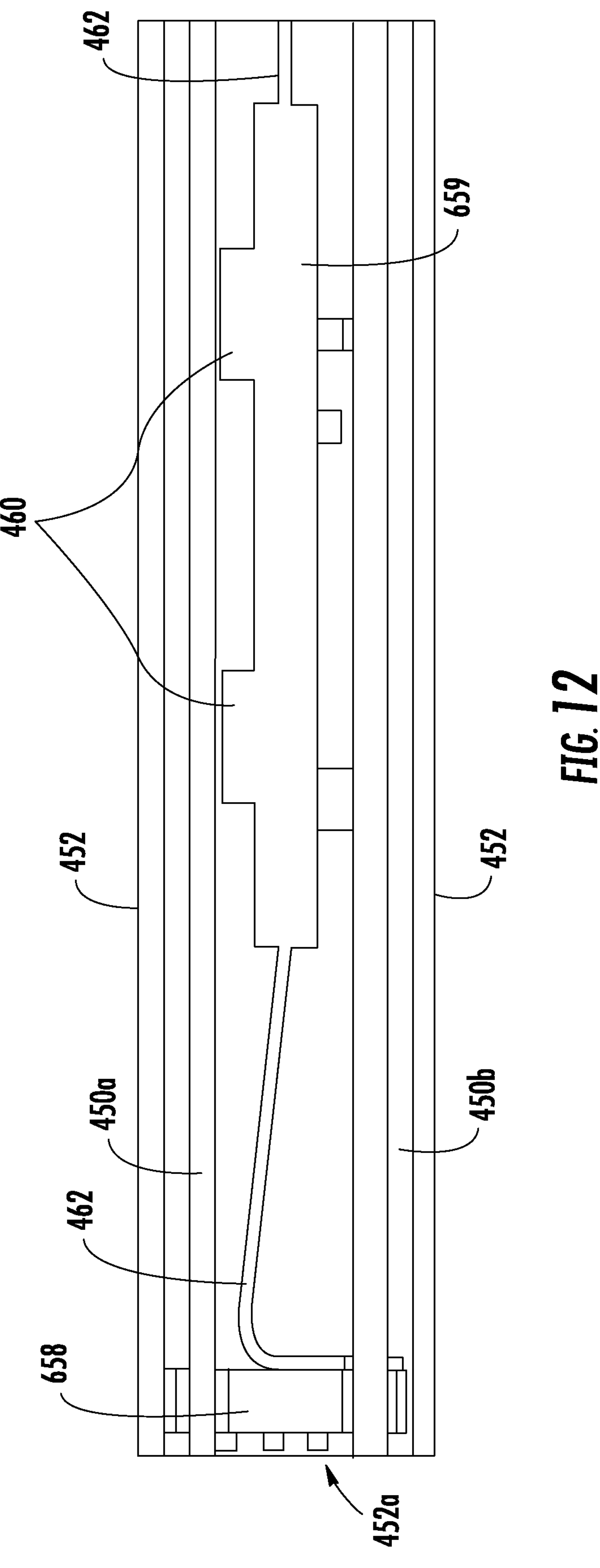

FIGS. 10, 11, and 12 show a first perspective view, a second perspective view, and a cross-sectional view of sensor head 457 in an implementation. End portions of light guides 450*a* and 450*b* are shown positioned in the apertures formed in PCB 658. Ends of the light guides can extend from the apertures, be positioned in the apertures, or be positioned behind the apertures.

The TIAs 460 are positioned between the light guides on a PCB 659, which is electrically connected between two analog wire bundles 462. A first of the analog wire bundles is electrically connected between PCB 658 and PCB 659 and a second of the analog wire bundles is connect between PCB 659 and coupler 417 or can extend into the reusable handpiece. The second of the analog wire bundles provides power, ground, control signals, or any combination of these from the reusable handpiece through the laparoscopic element to the PCB 659 and the TIAs, and transmits signals from the TIAs back to the reusable handpiece.

The first of the analog wire bundles provides power, ground, and control signal through the laparoscopic element from PCB 659 to the photodetectors, and provides detector signals generated by the photodetectors to the TIA for further transmission through the second of the analog wire bundles to the ADCs in the reusable handpiece.

PCB 659 has a first surface one with one or more of the TIAs are mounted, and has a second surface that is parallel to the first surface. Other electrical elements can be mounted on the second surface of PCB 659. The first and second surfaces are parallel to the lateral direction that the laparoscopic probe extends along. PCB 659 can be closer to the distal end of the laparoscopic element, where the sensor head is located at the distal end of the laparoscopic element, than to the proximal end of the laparoscopic element, where the laparoscopic element connected to the probe unit.

This application describes some examples of implementations with specific dimensions, measurements, and values. These are not intended to be exhaustive or to limit the invention to the precise form described.

The measurements are, for example, in millimeters or centimeters are approximate values. The values can vary due to, for example, measurement or manufacturing tolerances or other factors (e.g., plus or minus 5 percent, plus or minus 10 percent, plus or minus 15 percent, or plus or minus 20 percent). Further, the measurements are for a specific implementation of the device, and other implementations can have different values, such as certain dimensions made longer to accommodate larger hands or to access tissue in a particular location of the body.

For the specific implementations described, some specific values, ranges of values, and numbers are provided. These values indicate, for example, dimension, angles, ranges, frequencies, wavelengths, numbers, a relationship (e.g., relative value), and other quantities (e.g., numbers of sensors, sources, detectors, diodes, fiber optic cables, and so forth). Some measurements are for a specific implementation of the device, and other implementations can have different values, such as certain dimensions made larger for a larger-sized product, or smaller for a smaller-sized product. The device may be made proportionally larger or smaller by adjusting relative measurements proportionally (e.g., maintaining the same or about the same ratio between different measurements). In various implementations, the values (or numbers or quantities) can be the same as the value given, about the same of the value given, at least or greater than the value given, or can be at most or less than the value given, or any combination of these. The values (or numbers or quantities) can also be within a range of any two values given or a range including the two values given. When a range is given, the range can also include any number within that range to any other number within that range.

In an implementation, the diameter of the sensor head (e.g., diameter of PCB 658) is from about 3 millimeters to about 10 millimeters. In another implementation, the diameter of the sensor head (e.g., diameter of PCB 658) is from about 2 millimeters to about 10 millimeters. In a specific implementation, the diameter of the sensor head is approximately 5 millimeters, but can be other diameters. A sensor head having a diameter of 5 millimeters or less may have apertures for the source light guides and the detector light guides. In an implementation, a diameter is 5 millimeters or greater. In an implementation where the photodetectors are positioned on PCB 568 and light guides 150 extend through apertures in the PCB, the diameters of the sensor head is approximately 7 millimeters, but can be other diameters. In other implementations, the diameter cam be 7 millimeters or less, or 7 millimeters or greater.

A cross-sectional dimension (e.g., diameter of a round or circular cross-section dimension) of the central opening of the laparoscopic element can have similar lengths, such as about 2 millimeters to about 10 millimeters to accommodate a sensor head having a diameter of about 3 millimeters to about 10 millimeters. A wall thickness of the walls of the laparoscopic element range from about 0.5 millimeters to about 5 millimeters.

The outside cross-sectional dimension of the laparoscopic element can range from about 3 millimeters to about 20 millimeters or greater (e.g., 3, 4, 5, 6, 7, 8, 9, 10, 15, or 10 millimeters, or others.) The length of the laparoscopic element can range from about 10 centimeters to about 60 centimeters (e.g., 15, 20, 21, 22, 23, 24, 25, 26, 27, 28, 29, 30, 31, 32, 33, 34, 35, 36, 37, 38, 39, 40, or 45 centimeters (e.g., for bariatric procedures), or others).

A relationship between the probe unit and the laparoscopic element is that a width of the cross section of the laparoscopic element (e.g., 3 millimeters, 5 millimeters, or 10 millimeters) is less than a cross section the probe unit (e.g., 18 millimeters, 40 millimeters, 75 millimeters, or 95 millimeters). A ratio of cross-sectional width (or cross-section area) between probe unit and laparoscopic element can range from about 32:1 to about 1.8:1. For example, the ratio can be 2:1, 3:1, 4:1, 5:1, 6:1, 10:1, 16:1, 20:1, 24:1, or 30:1, or others value, or any value greater than or less than these (e.g., 2:1 or greater, 3:1 or greater, or 4:1 or greater, or 30:1 or less, 24:1 or less, or 5:1 or less), or in a range between these.

Also a cross-section shape can differ between the probe unit and the laparoscopic element. The cross section shape of the laparoscopic element can be, for example, a circle, ellipse, oval, or any rounded polygon (e.g., rounded square or rectangle). The cross section shape of the probe unit can be a circle, ellipse, oval, any polygon (e.g., rectangle, pentagon, hexagon, or octagon), or any rounded polygon. In an implementation, the cross-section shape of the laparoscopic element is a circle while the cross-section shape of the probe unit is a rounded rectangle. The cross-section shape of the laparoscopic element is a circle while the cross-section shape of the probe unit is also a circle, with a larger diameter or cross-section area. In an implementation, a volume of the probe unit will be greater than that of the laparoscopic element.

Also a material can differ between the probe unit and the laparoscopic element. For example, the material of the laparoscopic element can be a metal while the probe unit is a plastic (or other nonmetal or nonconductor). The material of the laparoscopic element can be a metal (e.g., stainless steel) while the probe unit is a polymer or composite. In an implementation, the probe unit and the laparoscopic element can both be metal, such as the same metal or different metals: both stainless steel, probe unit is aluminum or titanium while laparoscopic element is stainless steel. In other implementations, the laparoscopic element is titanium. The laparoscopic element can also be coated, such as with a polymeric coating to make the surface nonconductor.

The wall of the laparoscopic element can be formed from one or more of a variety of materials including metal (e.g., stainless steel, titanium, others), plastic, composite, carbon fiber, or others. The outer surface of the wall of the laparoscopic element is smooth for smooth movement in the trocar and tissue and for sterilization.

The tip of the laparoscopic element can have a variety of shapes, such as blunt or rounded. In an implementation, the tip of the laparoscopic element is not transverse with respect to the lateral extent of the tube of the element. That is, the probe face of the sensor head is not transverse to the lateral extent of the tube of the element. In an implementation, source structures and detector structures are positioned along the sides of the laparoscopic element so that the structures can make contact with target tissue when the tip cannot make contact with target tissue or such contact is difficult to make with the tip. In some embodiment, the sensor head is flush with the end of the laparoscopic tube, recessed within the laparoscopic tube, or extends from the laparoscopic tube.

In an implementation, probe unit 105 generally has a cross-sectional width that is wider than the laparoscopic element. The width tapers down from a proximal end to a distal end, where the probe unit mates or fits together with a proximal end of the laparoscopic element. At its widest cross section at the proximal end, the probe unit has a width of from about 75 millimeters to about 95 millimeters, which will accommodate a printed circuit board of about this size. Between the proximal and distal end, a widest width is about 40 millimeters, which will accommodate a printed circuit board of about this size. At the distal end, a widest width is about 18 millimeters, which will accommodate a printed circuit board of about this size.

A length of the probe unit from proximal to distal end is about 165 millimeters (where the widest width is from about 75 millimeters to 95 millimeters), from a middle to the distal end is about 105 millimeters (where the widest width is about 40 millimeters), and closer to the distal end, about 45 millimeters (where the widest width is about 18 millimeters). In some implementations, the probe unit can have a length from about 5 millimeters to about 10 millimeters.

The cross-section dimension of the outside of the laparoscopic element is less than the width of the widest of the probe unit in an implantation. The cross-section dimension of the outside of the laparoscopic element is also less than the width of the narrowest of the probe unit in an implantation.

The outer housing of the probe unit can be formed of the same or different material as the laparoscopic element. The outer housing of the probe unit can be formed from one or more of a variety of materials including metal (e.g., stainless steel, titanium, others), plastic, composite, or others.

FIG. 13 shows a block diagram of an oximetry system 1300 that includes an oximeter probe 1301 and a display 615 in an implementation. Oximeter system 1300 differs from oximeter system 600 in that TIAs 460 are located in the probe unit rather than in the laparoscopic element.

Oximeter probe 1301 can have a form factor similar to oximeter probe 101, 201, 301, or have other form factors. Probe unit 1305 and laparoscopic element 1308 can be separable or nonseparable. In an implementation where the oximeter probe is an integrated device that is non-separable, the oximeter probe can be a disposable unit that may be disposed of after use with a single patient. Where the oximeter probe and laparoscopic probe unit are separable, the oximeter probe can be reusable and the laparoscopic element can be a disposable unit that may be disposed of after use with a single patient.

The operation of oximetry system 1300 is similar to the operation of oximetry system 600 described above. However, detector signals generated by the photodiodes are transmitted through analog wire bundles 462 and 461 to the TIAs located in the probe unit. In an implementation, the probe unit includes display 115 (not shown), which can display the oximetry information generated by the oximeter probe.

Figure 14:
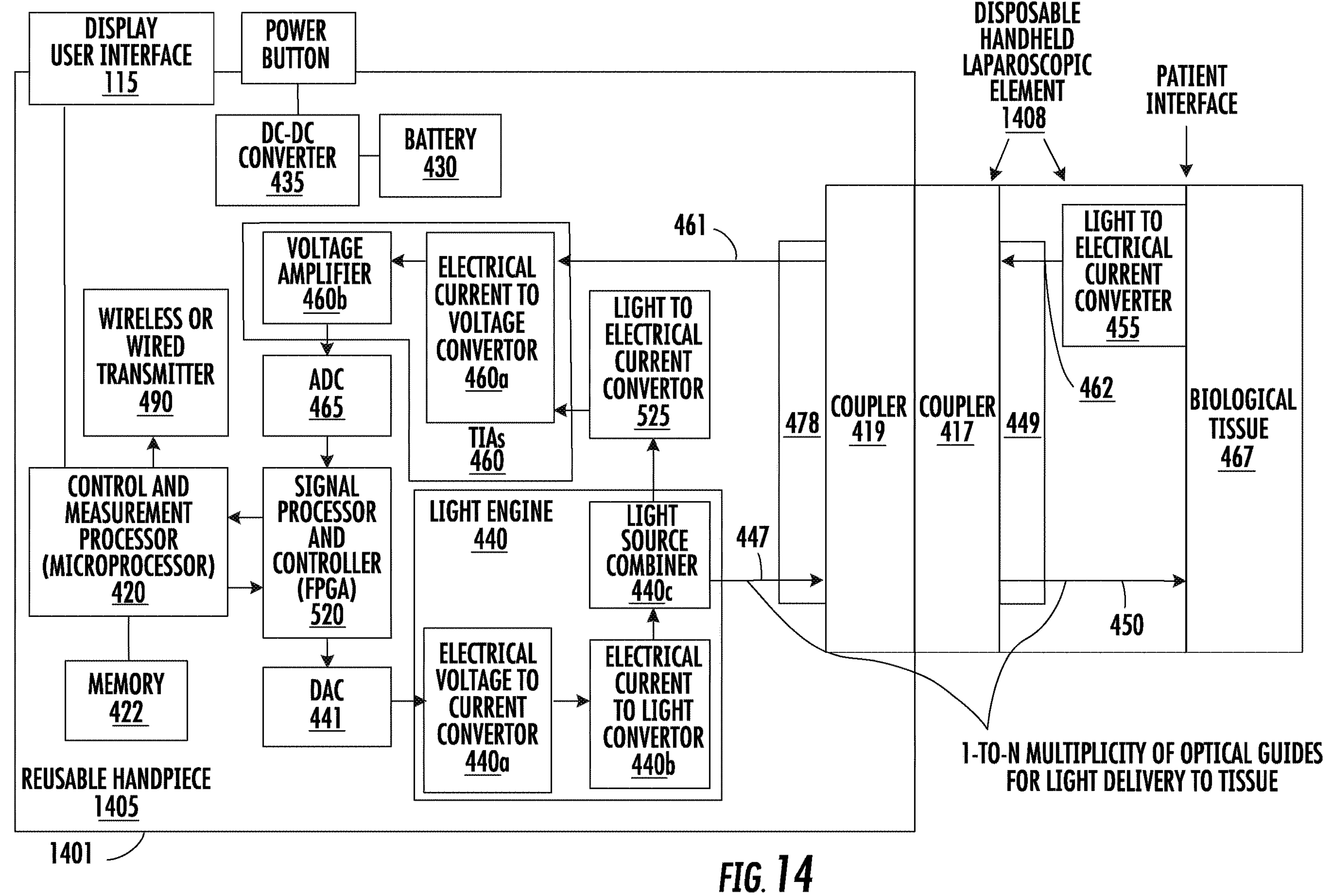
FIG. 14 shows an oximeter probe in an implementation.

FIG. 14 shows an oximeter probe 1401 in an implementation. Oximeter probe 1401 includes a probe unit 1405 and a laparoscopic element 1408. The oximeter probe is adapted to communicate with a display, such as display 615 described above. Oximeter probe 1401 is similar to oximeter probe 1301 but differs in that probe unit 1405 of the oximeter probe includes a signal acquisition processor 520 that is adapted to receive digitized detector responses for oximetry measurements from the ADCs 465 and preprocess the digitized detector responses for subsequent transmission to processor 420.

Probe unit 1405 can include a display 115. Some implementations of the probe unit do not include a display. The display of probe unit 1405 can display similar or different oximetry information than detached display 615.

Figure 15:
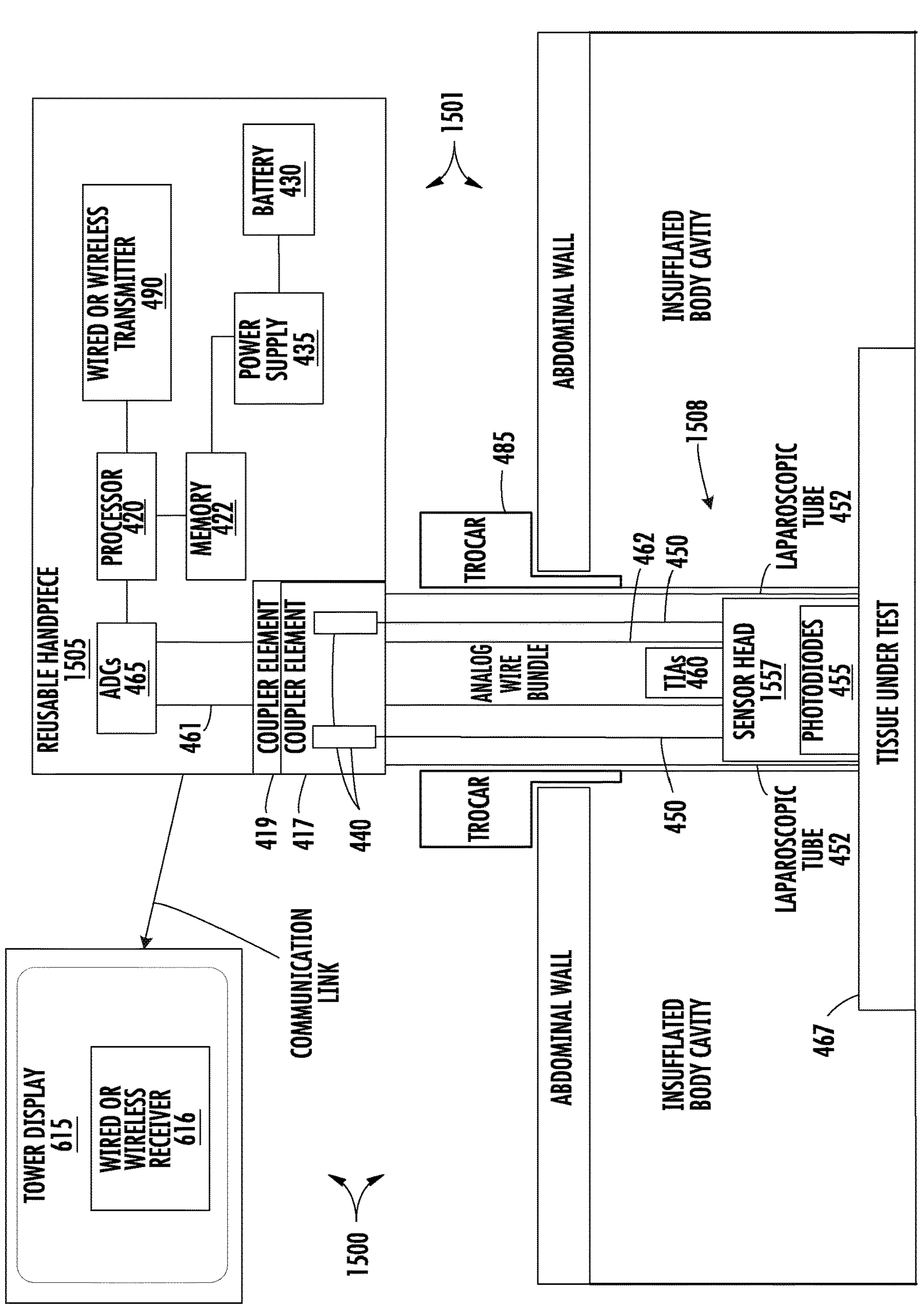
FIG. 15 shows a block diagram of an oximetry system that includes an oximeter probe and a display in an implementation.

FIG. 15 shows a block diagram of an oximetry system 1500 that includes an oximeter probe 1501 and a display 615 in an implementation. Oximeter probe 1501 includes a probe unit 1505 and a laparoscopic element 1508. The operation of oximetry system 1500 is similar to the operation of oximetry system 1300 described above. Oximeter system 1500 differs, however, from oximeter system 1300 in that light engine 440 is located in probe unit 1505, but is separable from the probe unit. Couplers 417 and 419 facilitate the releasable connection of the light engine into the probe unit. Couplers 417 and 419 also facilitate electrical connection of analog wire bundles 461 and 462.

Oximeter probe 1501 can have a form factor similar to oximeter probe 101, 201, 301, or have other form factors. The probe unit can be reusable and the laparoscopic element can be separated from the probe unit and disposed of after use.

Figure 16:
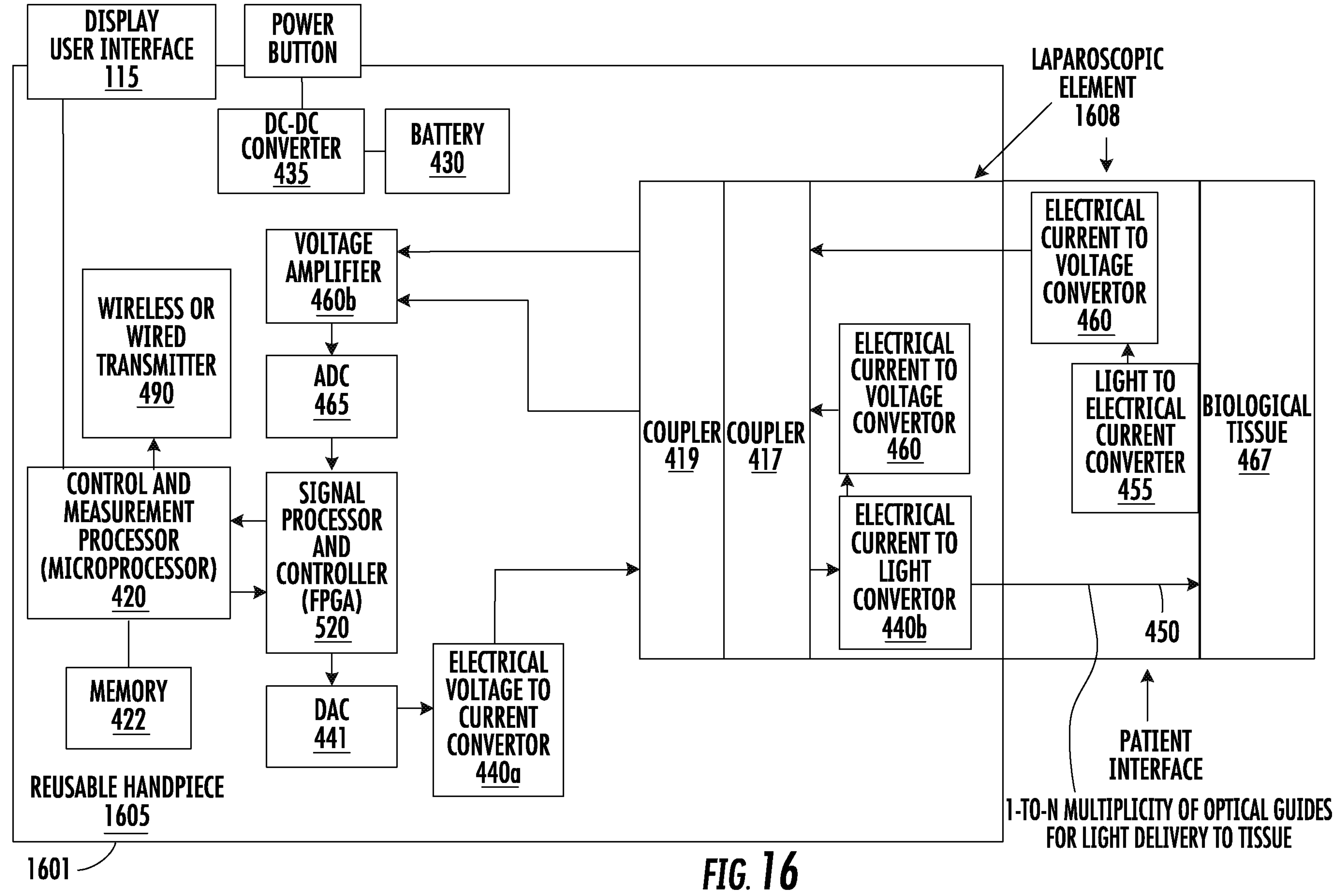
FIG. 16 shows an oximeter probe in an implementation.

FIG. 16 shows an oximeter probe 1601 in an implementation. Oximeter probe 1601 includes a probe unit 1605 and a laparoscopic element 1608. The probe unit is adapted to communicate with a display, such as display 615 described above. Oximeter probe 1601 is similar to oximeter probe 1401 but differs in that probe unit 1605 includes a signal acquisition processor 520 that is adapted to receive digitized reflection data for oximetry measurements from the ADCs 465 and preprocess the digitized reflection data for subsequent transmission to processor 420 for subsequent processing.

Voltage amplifier **460*b*, which is electrically connected between current to voltage convertor 460*a* and ADC 465, can be housed in the probe unit 1605 or housed in the laparoscopic element 1608. Similarly, the voltage to current convertor 460*a* or the light engine (e.g., convertor 440*a* and LEDs 440*b***) can be housed in the probe unit or in the laparoscopic element.

Probe unit 1605 can include display 115. Some implementations of the probe unit do not include a display. The display of probe unit 1605 can display similar or different oximetry information than detached display 615.

FIG. 17 shows a block diagram of an oximetry system 1700 that includes an oximeter probe 1701 and a display 615 in an implementation. Oximeter probe 1701 includes a probe unit 1705 and a laparoscopic element 1708. The operation of oximetry system 1700 is similar to the operation of oximetry system 1500 described above. Oximeter system 1700 differs, however, from oximeter system 1500 in that TIAs 460 and photodetectors 455 are housed in probe unit 1705. The photodetectors are optically connected to optical port 449 and may be connected to the port by a set of light guides 480. Light engine 440 is also optically connected to optical port 499 and may be connected to the port by light guides 447.

Laparoscopic element 1708 includes light guides 450 and 464. Optical ports 449 and 478 when connected, in-turn optically connect light guides 480 and 464 and optically connect light guides 447 and 450. The optical ports can be optically connected by the connection of coupler elements 417 and 419. In some implementations, each optical port and its associated coupler elements are integrated elements.

Light emitted from the LEDs in the light engine is transmitted into light guides 447 and thereafter is transmitted through light guide 477 to light guides 450. Light transmitted through light guides 450 is transmitted to the sensor head and can thereafter be transmitted out from the sensor head into tissue 467 to be examined.

Light collected by the sensor head is transmitted through light guides 464 to light guides light guides 480. Light guides 480 transmit the light to photodetectors 455. The photodetectors generate detector responses that are amplified by the TIAs and transmitted from the TIAs to the ADCs. The ADCs digitize the analog detector responses output from the TIAs and transmit digitized detector responses for the collected light to the processor. The processor can determine a variety of information for the tissue under test based on the detector responses, such as absolute StO2, relative StO2, total hemoglobin, blood volume, or other information. The oximetry information is then transmitted from the oximeter probe to the display for display. Other function performed by oximetry system 1700 and oximeter probe 1701 are described above with respect to other oximetry probe implementations.

Figure 18:
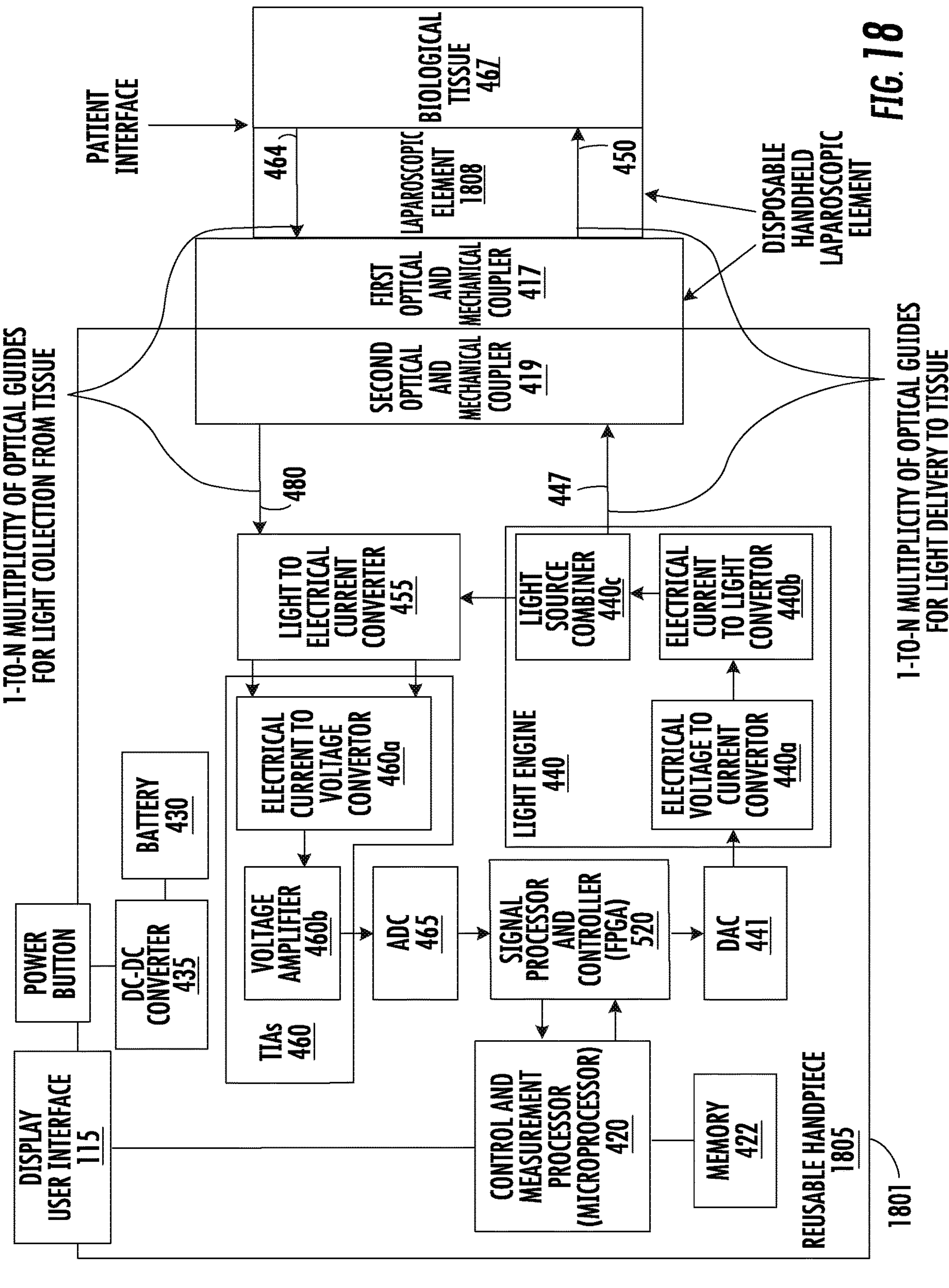
FIG. 18 shows an oximeter probe in an implementation.

FIG. 18 shows an oximeter probe 1801 in an implementation. Oximeter probe 1801 includes a probe unit 1805 and a laparoscopic element 1808. The probe unit is adapted to communicate with a display, such as display 615 described above. Oximeter probe 1801 is similar to oximeter probe 1701 but differs in that probe unit 1805 includes a signal acquisition processor 520 that is adapted to receive digitized information for oximetry measurements from the ADCs 465 and preprocess the digitized information for subsequent transmission and processing by processor 420.

Probe unit 1805 can include a display 115. Some implementations of the probe unit do not include a display. The display of probe unit 1805 can display similar or different oximetry information than detached display 615.

Figure 19:
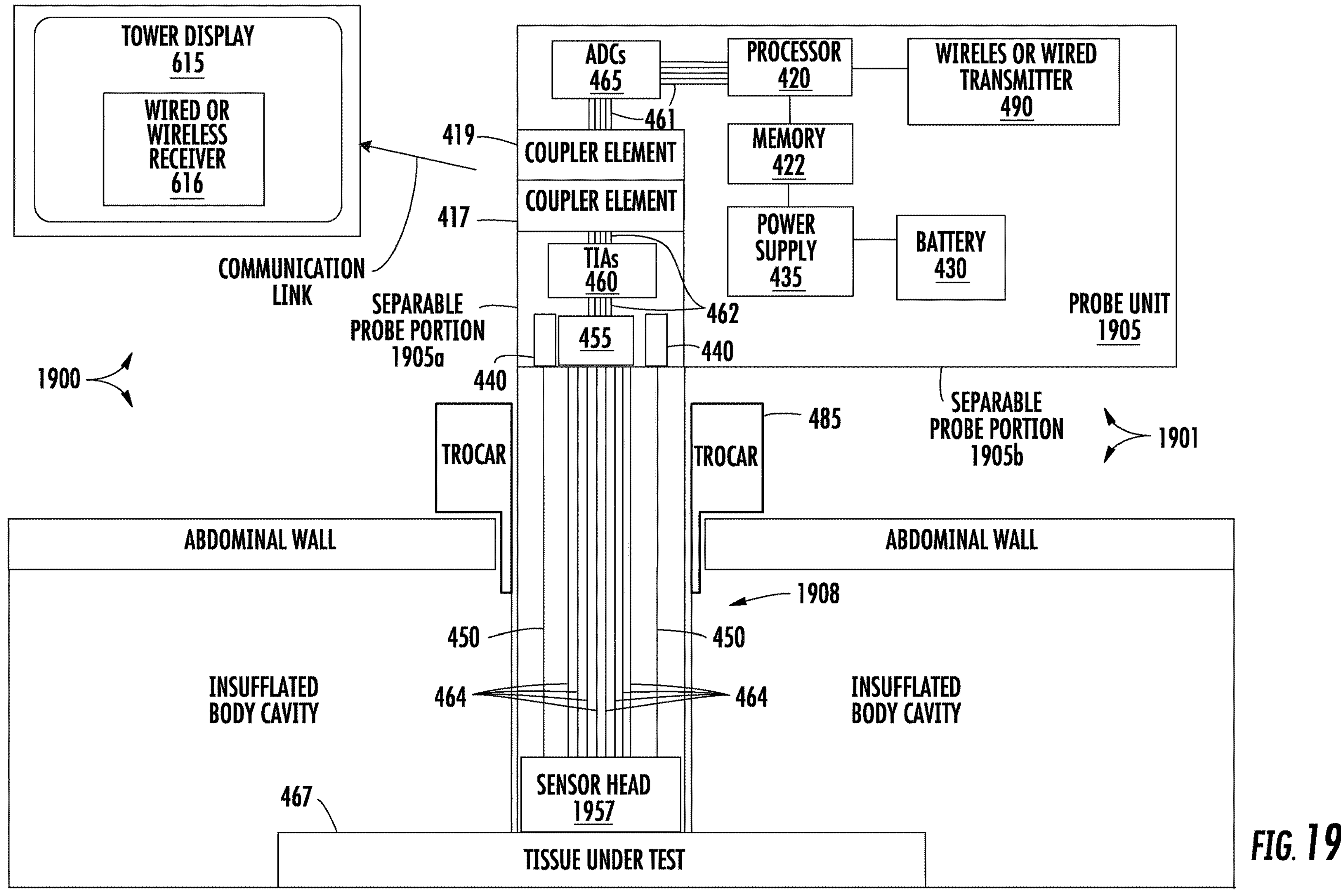
FIG. 19 shows a block diagram of an oximetry system that includes an oximeter probe and a display in an implementation.

FIG. 19 shows a block diagram of an oximetry system 1900 that includes an oximeter probe 1901 and a display 615 in an implementation. Oximeter probe 1901 includes a probe unit 1905 and a laparoscopic element 1908. Oximeter probe 1901 can have a form factor similar to oximeter probe 101, 201, 301, or have other form factors.

The operation of oximetry system 1900 is similar to the operation of oximetry system 1700 described above. Oximeter system 1900 differs, however, from oximeter system 1700 in that probe unit 1905 is formed of separable probe unit portions **1905*a* and 1905*b*. Probe unit portion 1905*a* houses light engine 440, photodetectors 455, and TIAs 460, and probe unit portion 1905*b* houses ADCs 465, processor 420, memory 422, transmitter 490, power supply 435, and battery 430. The portions of the probe unit can include additional or alternative electrical components not shown. The light engines 440 are closer to the top of the laparoscopic element than the bottom of the laparoscopic element, where the bottom of the laparoscopic element houses the sensor head. In an implementation, the light engines are housed in the coupler 417 element of the laparoscopic element. In an implementations, the light sources are in the sensor head 1957** where the light sources are closer to the bottom of the laparoscopic element than to the top of the laparoscopic element.

Coupler elements 419 and 417 can mechanically connect probe unit portions 1905*a* and 1905*b* and can electrically connect the electrical components in the probe unit portions. Specifically, the coupler components can electrically connect analog wiring bundles 461 and 462. Connection of the analog wire bundles electrically connects the TIAs in probe unit portion 1905*a* to the ADCs in probe unit portion 1905*b*. The connected analog wire bundles can also electrically connect other electrical components in the two portions of the probe unit, such as electrically connecting the processor to the light engine and connecting the power source and ground to the TIAs, the photodetectors, and the light engine.

In the implementation, probe unit portion 1905*a* is connected to laparoscopic element 1908. Probe unit portion 1905*a* and laparoscopic element 1908 can be disposable elements of the oximeter probe and the probe unit can be reusable.

The laparoscopic element includes light guides 450 and 464, which are optically connected, respectively, to the light engines and the photodetectors. Light emitted from the LEDs in the light engine is transmitted into light guides 450 and thereafter is transmitted through light guides 450 to the sensor head. The light can be transmitted out from the sensor head into tissue 467 to be examined.

Light collected by the sensor head is transmitted through light guides 464 to photodetectors 455. The photodetectors generate detector responses that are amplified by the TIAs and transmitted from the TIAs to the ADCs. The ADCs digitize the analog detector responses output from the TIAs and transmit the digitized detector responses for the collected light to the processor. The processor can determine a variety of information for the tissue under test based on the detector responses, such as absolute StO2, relative StO2, total hemoglobin, blood volume, or other information. The oximetry information is then transmitted from the oximeter probe to the display for display. Other function performed by oximetry system 1900 and oximeter probe 1901 are described above with respect to other oximeter probe implementations.

Figure 20:
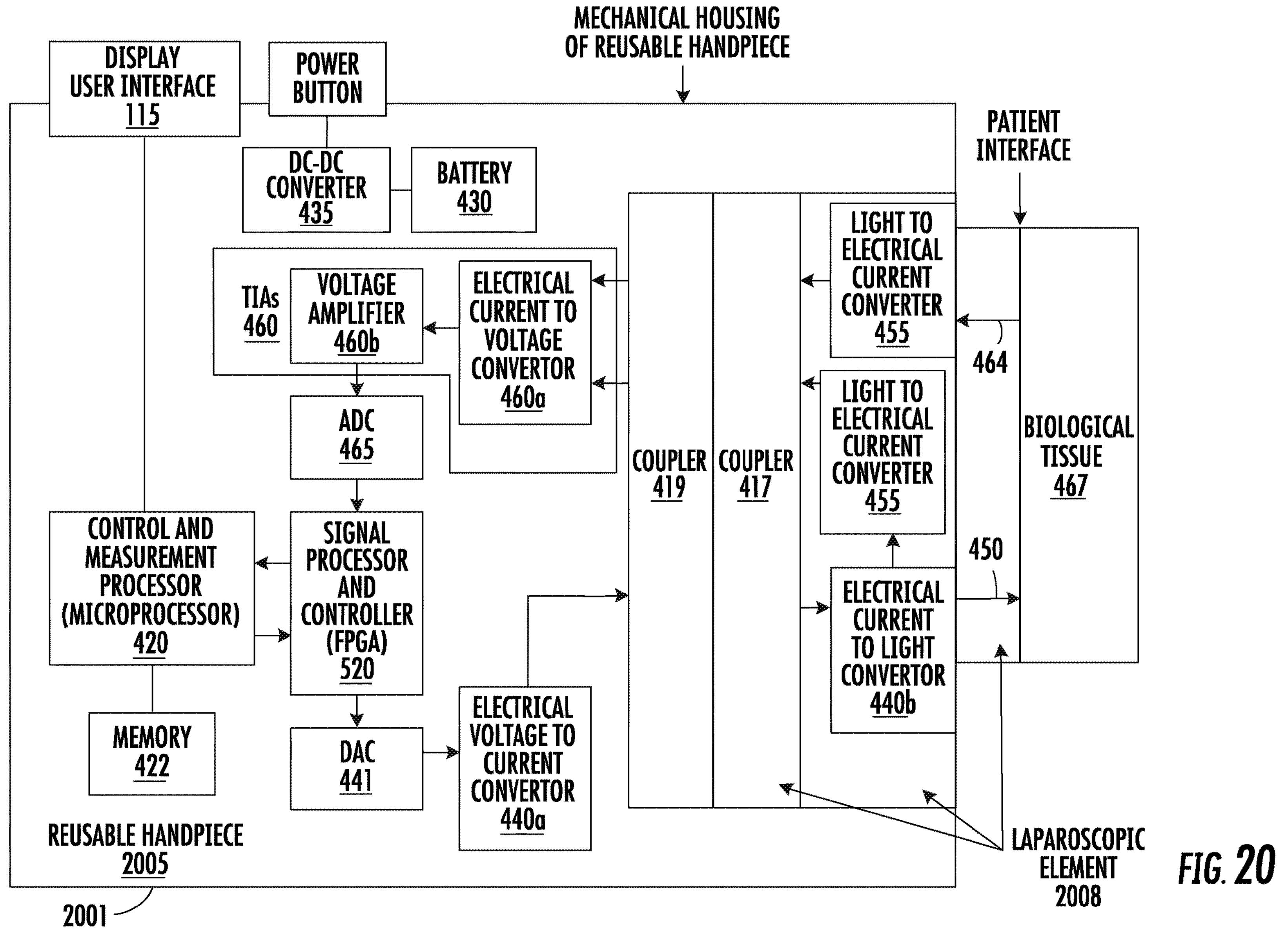
FIG. 20 shows an oximeter probe in an implementation.

FIG. 20 shows an oximeter probe 2001 in an implementation. Oximeter probe 2001 includes a probe unit 2005 and a laparoscopic element 2008. The probe unit is adapted to communicate with a display, such as display 615 described above. Oximeter probe 2001 is similar to oximeter probe 2001 but differs in that probe unit 2005 includes a signal acquisition processor 520 that is adapted to receive digitized information for oximetry measurements from the ADCs 465 and preprocess the digitized information for subsequent transmission and processing by processor 420.

Probe unit 2005 can include a display 115. Some implementations of the probe unit do not include a display. The display of probe unit 2005 can display similar or different oximetry information than detached display 615.

Figure 21:
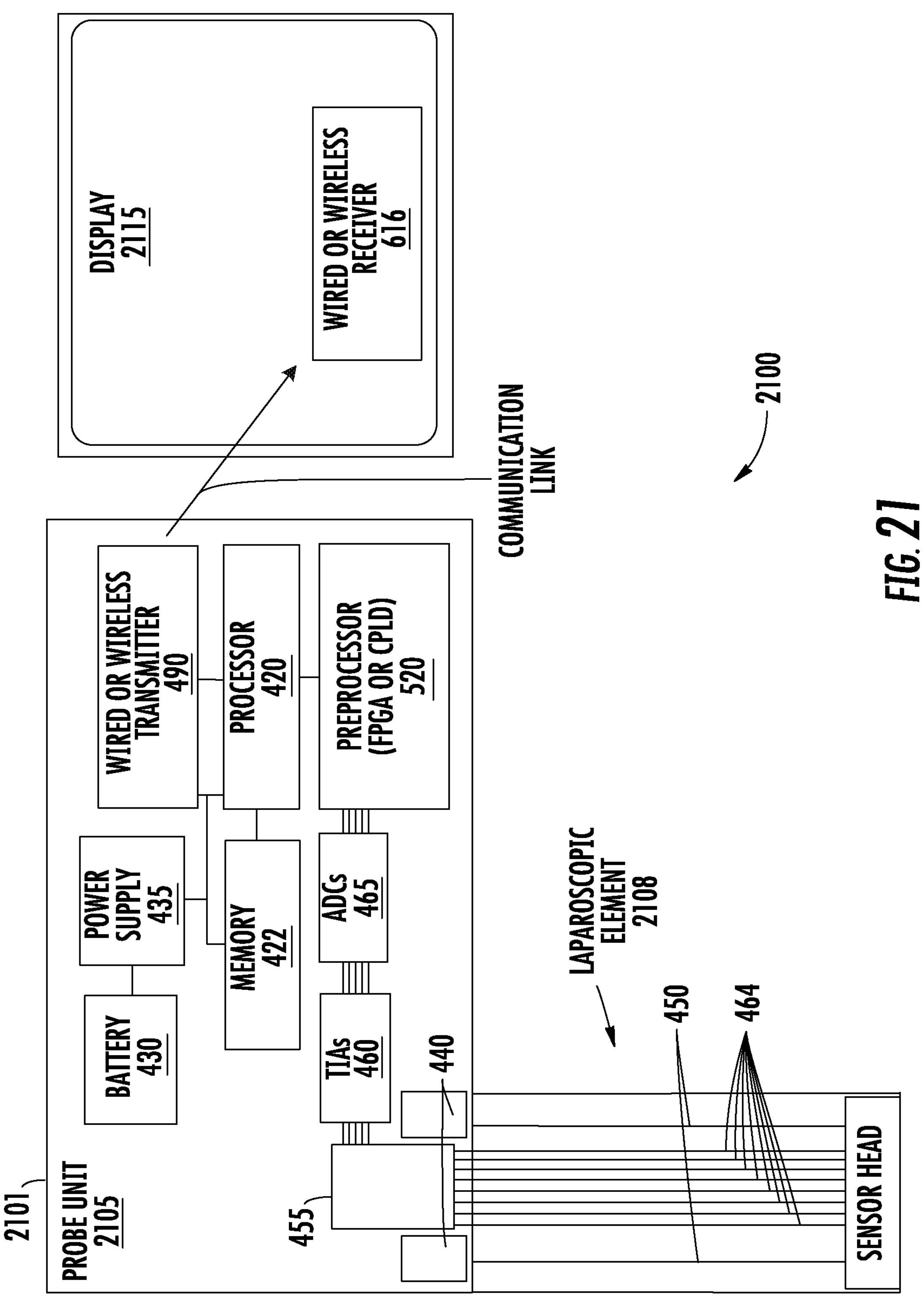
FIG. 21 shows a block diagram of an oximetry system that includes an oximeter probe and a display where a transmitter in the probe is electrically connected to the processor of the probe.

FIG. 21 shows a block diagram of an oximetry system 2100 that includes an oximeter probe 2101 and a display 2115 in an implementation. Oximeter probe 2101 includes a probe unit 2105 and a laparoscopic element 2108. Oximeter probe 2101 can have a form factor similar to oximeter probe 101, 201, 301, or have other form factors. The oximeter probe can have one or more combinations of the optical and electrical components described above for oximeter probe 101, 401, 501, 601, 701, 1301, 1401, 1501, 1601, 1701, 1801, 1901, or other combinations of configurations of optical and electrical components. The laparoscopic element of the oximeter probe can be separable or not separable from the probe unit facilitating reusability of the probe unit, the laparoscopic element, or both. The oximeter probe can have an integrated display, can be adapted to use a separate display, such as display 2115, or can use both displays to display oximetry information. Display 2115 includes a power source, such as a battery power source, that is a different battery source than the power source in the probe unit. The power source in the display 2115 is electrically connected to the electronic unit in the display and powers the electronic units, such as the receiver, the integrated display, and others, such as a processor, a preprocessor, or a memory.

Processor 420 of the oximeter probe is electrically connected between preprocessor 520 and transmitter 490. The preprocessor is adapted to receive digitized detector responses from the ADCs that digitize the analog detector responses generated by the detectors in response to light collected by the detectors. The preprocessor is adapted to preprocess the digital data prior to transferring the preprocessed data to the processor for additional processing, such as final processing.

The preprocessor is adapted to transfer the preprocessed data to the processor for additional processing, such as determining absolute StO2, relative StO2, total hemoglobin, blood volume, or other information. The processor thereafter transfers the processed data to the transmitter for transmission to the display. The processor, the transmitter, or other circuits can be adapted to packetize the processed data for transmission. The receiver after receipt of the processed data can then display one or more pieces of oximetry information received from the transmitter.

The transmitter and receiver can each be adapted for wired communications (e.g., cable communications), wireless communications, or both wired and wireless communications. The transmitter and receiver can be adapted to operate according to one or more of a variety of transmission protocols, such as one of the Bluetooth® protocol of the Bluetooth SIG, Inc. of Kirkland Washington, the WirelessHD™ protocol of the Lattice Semiconductor Corporation of Portland Oregon, Wi-Fi, Ethernet, or other protocols.

The probe unit (e.g., first probe unit) is replaceable with a second probe unit that is a different probe unit from the first probe unit in an implementation. The first probe unit is disconnectable from the display, such as via the wired connection between the first probe unit and the display being physically disconnected from one or both of these elements, via the wired connection be turned off via a switch (e.g., a software switch or a hardware switch).

The first probe unit is disconnectable from the display, such as via the wireless connection between the first probe unit and the display being physically disconnected from one or both of these elements, via the wireless connection be turned off via a switch (e.g., a software switch or a hardware switch). For example, if the first probe unit and the display are adapted for using a Bluetooth protocol, the Bluetooth link can be disconnected from the probe unit, the display, or both.

The second probe unit can thereafter be connected to the display via a wired connection or a wireless connection. The wireless connection can be any of the wireless connection described in the this patent, such as Bluetooth protocols (Bluetooth, Bluetooth SMART, Bluetooth Low Energy, others), one of the IEEE 802.11 protocols, ANT, 6LoWPAN, MyriaNed, EnOcean, Z-Wave, Wi-Fi, one of the IEEE 802.15.4 protocol, such as ZigBee, or others. Thereafter, the second probe unit can operate the same or similar to the first probe unit as described in this patent.

The second probe unit is configured the same or similarly as the first probe unit and can generate measurement information for tissue and transfer the measurement information to the display where the display determines (e.g., via one or more spatially resolved spectroscopy techniques) various oximetry values from the oximetry information, such as an absolute StO2 value, a relative StO2 value, a total hemoglobin value, a blood volume value, a percentage of oxygenated hemoglobin (HbO2) value, a percentage of deoxygenated hemoglobin (Hb) value, a melanin concentration value, or other oximetry values.

Figure 22:
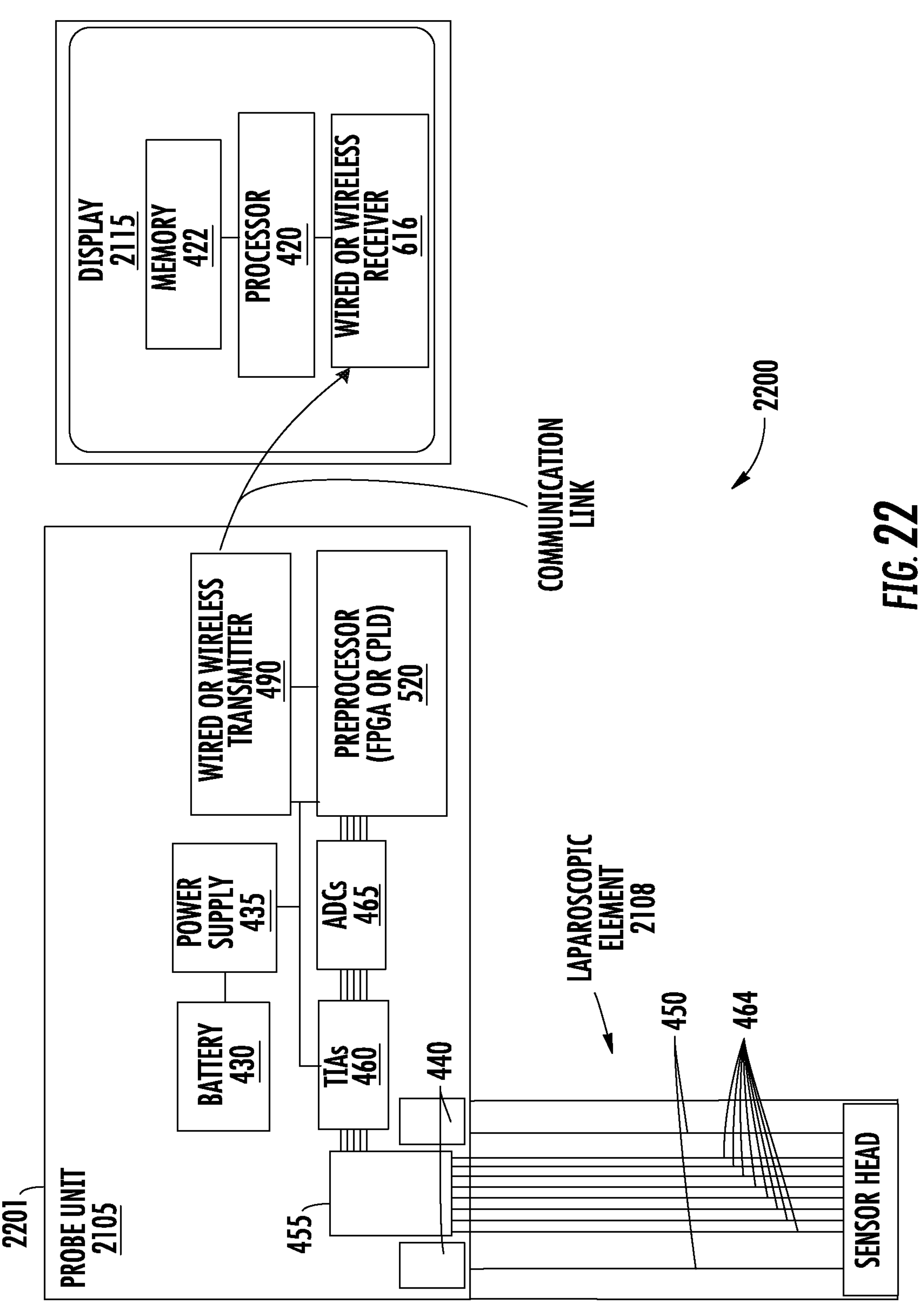
FIG. 22 shows a block diagram of an oximetry system that includes an oximeter probe and a display where a transmitter in the probe is electrically connected to the preprocessor of the probe and where the processor is located in the display.

FIG. 22 shows a block diagram of an oximetry system 2200 that includes an oximeter probe 2201 and a display 2215 in an implementation. Oximeter probe 2201 includes a probe unit 2205 and a laparoscopic element 2108. Oximeter probe 2201 can have a form factor similar to oximeter probe 101, 201, 301, or have other form factors. The oximeter probe can have one or more combinations of the optical and electrical components described above for oximeter probe 101, 401, 501, 601, 701, 1301, 1401, 1501, 1601, 1701, 1801, 1901, or other combinations of configurations of optical and electrical components. The laparoscopic element of the oximeter probe can be separable or not separable from the probe unit. The oximeter probe can have an integrated display, be adapted to use a separate display, or both.

Oximetry system 2200 is similar to oximeter system 2100 described above, but differs in that transmitter 490 is electrically connected to preprocessor 520 in probe unit 2205, and processor 420 and memory 422 are housed in display 2115. The preprocessor, processor, and memory are adapted to perform one or more of the functions described above for determining oximetry information. In an implementation, the oximetry information does not include a value for StO2 for tissue. In a further implementation, the oximetry information does not include a value for absolute StO2, relative StO2, total hemoglobin, blood volume, or other information.

The preprocessor, the transmitter, or other circuits, are adapted to packetize the preprocessed data (e.g., digitized data). Thereafter, the preprocessor can transfer the packetized data to the transmitter for transmission to receiver 616 housed in the display.

The transmitter and receiver can each be adapted for wired communications, wireless communications, or both wired and wireless communications and can be adapted to communicate via one or more of a variety of transmission protocols.

Processor 420, housed in the display, is adapted to receive the preprocessed data (e.g., digitized data) from the receiver and perform additional processing on the data, such as determining absolute StO2, relative StO2, total hemoglobin, blood volume, or other information. That is, the display is adapted to perform at least a portion of the processing of the oximetry data of the oximeter system for determining the oximetry information for display. In some implementation, the processor of the display can be a relatively "powerful" processor that can process final operations on the detector responses more quickly than the oximeter probe. After final processing, the display can display one or more pieces of oximetry information for the tissue.

In an implementation memory 422 stores executable code that is transferred from the memory to the processor for execution. The executable code is adapted for execution by the processor to perform spatially resolved spectroscopy steps to determine one or more of absolute StO2, relative StO2, total hemoglobin, blood volume, percentage of oxygenated hemoglobin (HbO2), the percentage of deoxygenated hemoglobin (Hb), melanin concentration, or other oximetry information. That is, the display is adapted to perform at least a portion of the spatially resolved spectroscopy processing of the oximetry data as described in this patent. For example, memory 422 can store the simulated reflectance curved used by the processor for fitting reflectance data to the curves for determining the absorption coefficients and scattering coefficients for the tissue to thereby determine oximeter information, such as absolute StO2, relative StO2, total hemoglobin, blood volume, HbO2, Hb, melanin concentration, or other information.

In an implementation, the display is included in a laparoscopic tower unit or includes a laparoscopic tower unit. With the display in a laparoscopic tower unit or including a laparoscopic tower unit, medical personal can view the display and the displayed oxygen saturation information displayed on the display while viewing other monitors that display views and information for the laparoscopic procedure being performed without the need to avert their eyes to a display that is not on the laparoscopic tower unit to view the oximetry information. In an implementation, the display is adapted to display views and information for the laparoscopic procedure being performed and display the oxygen saturation information.

In an implementation, when the probe unit is wire connected to the display, the wireless transmitter of the probe unit does not transmit oximetry information to the display via the wireless communication link. That is, the wireless transmitter can be disabled when the probe unit and display are wire connected for communication of oximetry information. In an implantation, both direct wired and wireless connections between the probe unit and display are used by these elements to exchange information.

In an implementation, the wired link between the oximeter probe and the display is a direct wired connection. That is, no intermediary wired transmitter circuits, wired receiver circuits, or wired transceiver circuits receive the wired signal transmitted from the oximeter probe for subsequent for retransmission of the wired signal to the display. Similarly, no intermediary transmitter circuits, receiver circuits, or transceiver circuits receive the wired signal transmitted from the display for subsequent for retransmission of the wired signal to the oximeter probe.

The display transmits emitter information to the probe unit. The probe unit uses the emitter information to control the emitters to emit light. The probe unit includes a digital-to-analog convertor (DAC) that transforms the emitter information in digital form to analog form for use by the emitters. The DAC is positioned between the transceiver 490 and the light engines 440. The emitter information is stored in the memory in the display and transmission of the emitter information to the probe unit is control by the processor.

Figure 23:
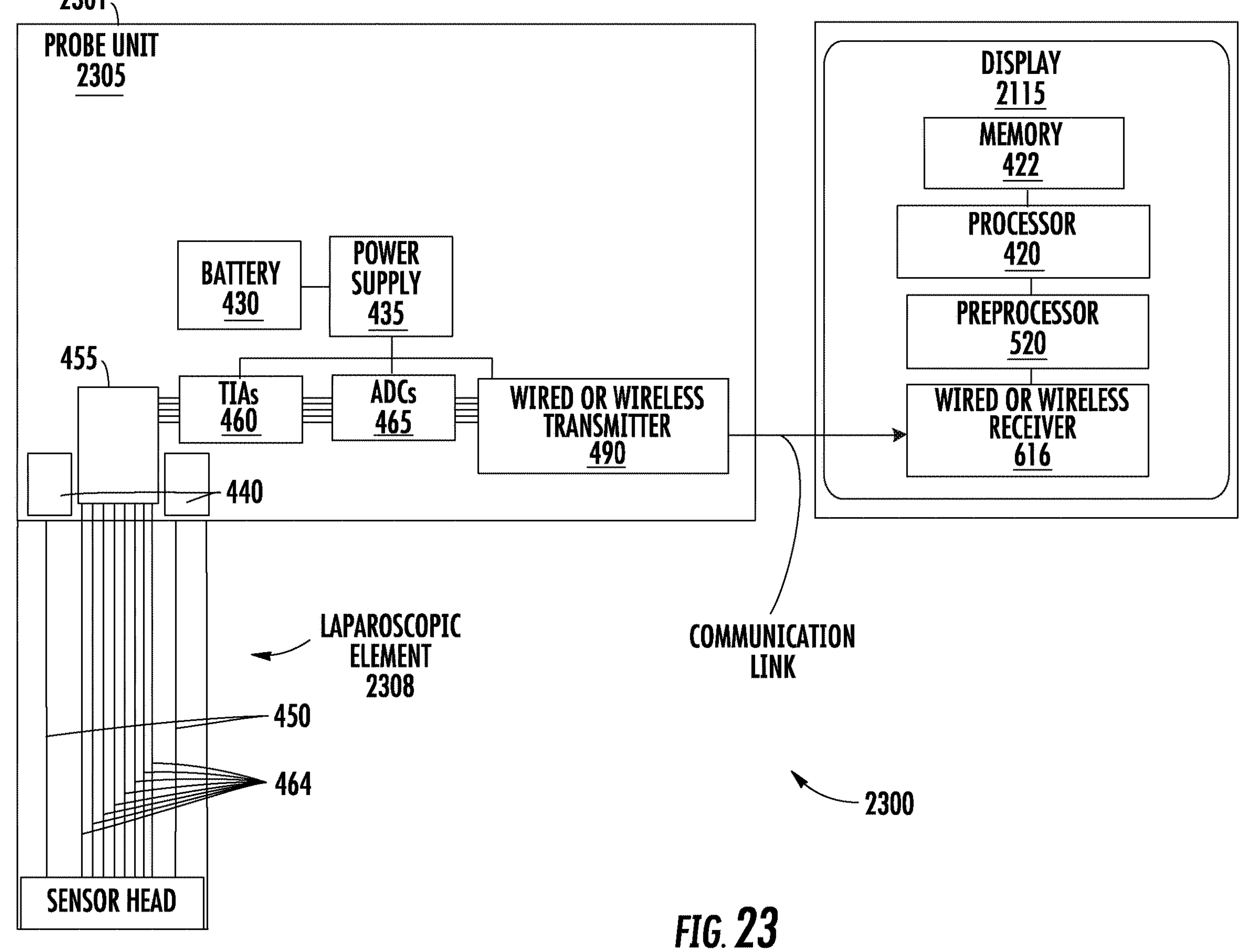
FIG. 23 shows a block diagram of an oximetry system that includes an oximeter probe and a display where a transmitter in the probe is electrically connected to the analog-to-digital convertors of the probe and where the preprocessor and processor are located in the display.

FIG. 23 shows a block diagram of an oximetry system 2300 that includes an oximeter probe 2301 and a display 2315 in an implementation. Oximeter probe 2301 includes a probe unit 2305 and a laparoscopic element 2308. Oximeter probe 2301 can have a form factor similar to oximeter probe 101, 201, 301, or have other form factors. The oximeter probe can have one or more combinations of the optical and electrical components described above for oximeter probe 101, 401, 501, 601, 701, 1301, 1401, 1501, 1601, 1701, 1801, 1901, or other combinations of configurations of optical and electrical components. The laparoscopic element of the oximeter probe can be separable or not separable from the probe unit. The oximeter probe can have an integrated display, can be adapted to use a separate display, or both.

Oximetry system 2300 is similar to oximeter systems 2100 and 2200 described above, but differs in that transmitter 490 is electrically connected to ADCs 465 in probe unit 2305, and preprocessor 520, processor 420 and memory 422 are housed in display 2315.

The ADCs are adapted to digitize the analog detector responses generated by the photodetectors and amplified by the TIAs. The ADCs then transfer the digitized detector responses to the transmitter for transmission to the receiver that is located in the display. The digitized detector responses provided by the ADCs are substantially raw data that undergoes little or no processing other than digitization. The digitized detector responses can be transmitted from the transmitter as a nonpacketized stream or a packetized stream. The ADCs, the transmitter, or other circuitry can packetize the digitized detector responses for transmission.

In an implementation, oximetry information that is digitized by the ADCs does not include a value for StO2 for tissue. In a further implementation, the oximetry information does not include a value for absolute StO2, relative StO2, total hemoglobin, blood volume, or other information.

The receiver, housed in the display, is adapted to receive the data transmitted by the transmitter. The preprocessor is electrically connected to the receiver and is adapted to receive the digitized detector responses from the receiver. Thereafter, the preprocessor, processor, and memory are adapted to perform the functions described above, such as preprocessing the digitized detector responses for generating oximetry information, such as determining absolute StO2, relative StO2, total hemoglobin, blood volume, or other information. The display can display one or more of these pieces of information or indicators (e.g., bar graph) for these pieces of information.

The transmitter and receiver can each be adapted for wired communications, wireless communications, or both wired and wireless communications, and operate according to one or more communication protocols.

Figure 24:
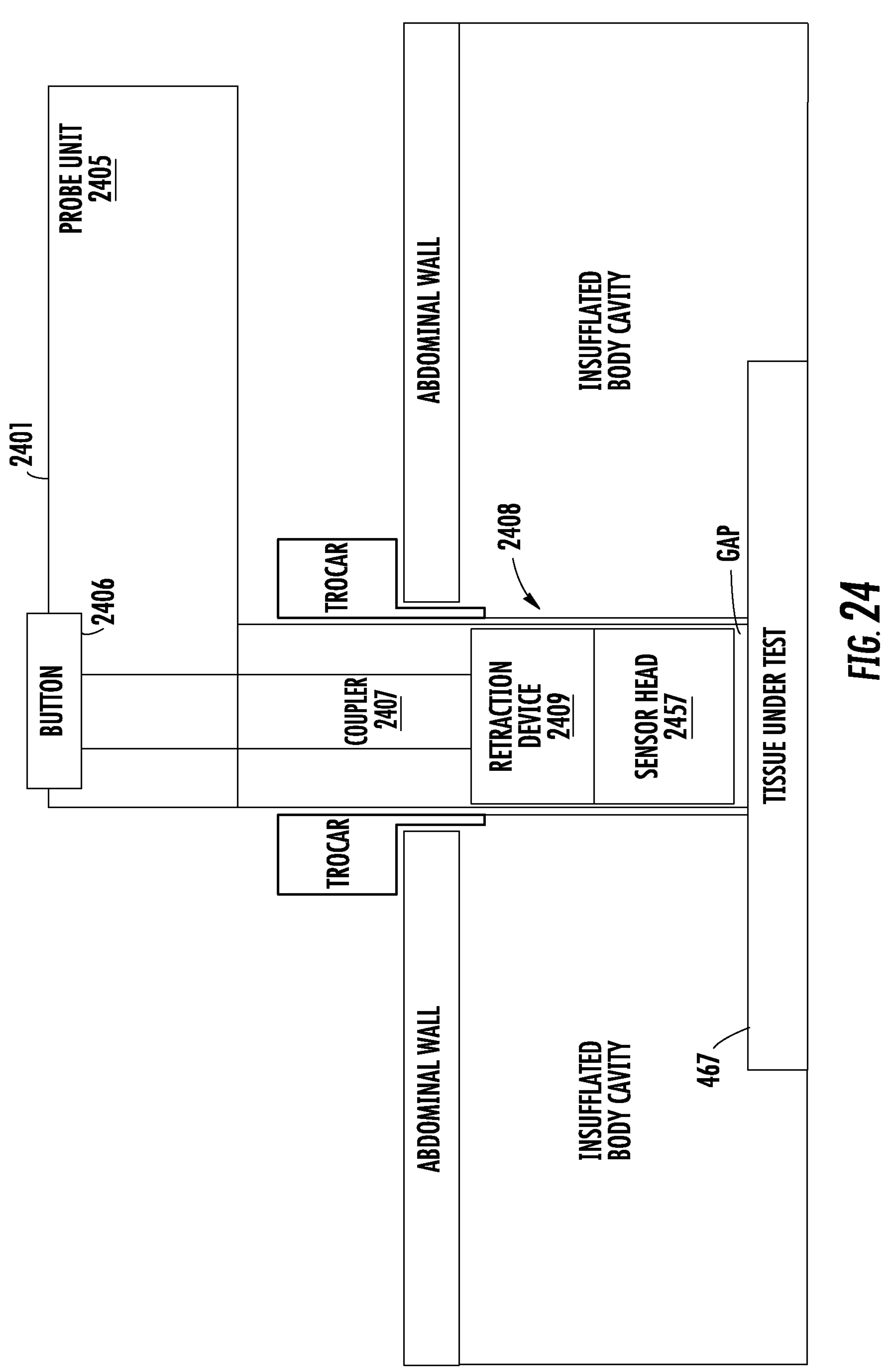
FIG. 24 shows a block diagram of an oximeter probe that includes a probe unit and a laparoscopic element where the sensor head is moved in the laparoscopic element by a button of the probe unit.

FIG. 24 shows a block diagram of an oximeter probe 2400 that includes a probe unit 2405 and a laparoscopic element 2408 in an implementation. Oximeter probe 2401 can have a form factor similar to oximeter probe 101, 201, 301, or have other form factors. The oximeter probe can have one or more combinations of the optical components and electrical components described above for oximeter probe 101, 401, 501, 601, 701, 1301, 1401, 1501, 1601, 1701, 1801, 1901, 2101, 2201, 2301, or other combinations of configurations of optical and electrical components. The laparoscopic element of the oximeter probe can be separable or not separable from the probe unit. The oximeter probe can have an integrated display or be adapted to use a separate display for displaying oximetry information.

The oximeter probe includes a user input device 2406, such as a push button, a slide button, or other device that is accessible from an external surface of the housing of the probe unit or laparoscopic element. The user input device is mechanically connected to the sensor head 2457 and is adapted to move the sensor head in the laparoscopic tube when the user input device is actuated to ensure tissue engagement. The user input device can be connected to the sensor head by a coupler 2407 that extends from the input device, though the reusable housing, and through the laparoscopic element to the sensor head. The coupler can be adapted to flex if the laparoscopic element is a flexible laparoscopic element (e.g., a nonrigid laparoscopic element).

In an implementation, the user input device, when actuated by a user, is adapted to move the coupler in the laparoscopic tube to move the sensor head from a first retracted position in the laparoscopic to a second position in the laparoscopic tube. In the second position, the sensor head can contact the tissue and can be used by the oximeter probe to emit light into the tissue and collect the light from the tissue for oximetry measurements.

The oximeter probe can include a retraction device 2409 (such as a spring) that retracts the sensor head from the second position to the first position. The retraction device can retract the sensor head to the first position when the input device is no longer actuated, such as when the button is released by a user. The retraction device can be connected to the input device, the coupler, the sensor head, or any combination of these elements.

The user input device can be adapted to releasably lock the sensor head in the second position after the user input device is actuated. The user input device can include a variety of locking devices that are adapted to lock the sensor head in the second position. The locking device allows the user to release pressure from the button and reduce hand fatigue while using the oximeter probe for an extended time, such as during a bowel resection or other long temporal procedure.

In an implementation, the oximeter probe includes a pressure sensor that detects the contact pressure of the sensor head against the tissue. The pressure sensor can be located on a probe face of the sensor head such that the pressure sensor can detect the pressure of the sensor head against the tissue. The pressure sensor can be electrically connected to the processor, the preprocessor, or both, and information for the detected pressure can be displayed on the display by the processor.

Figure 25:
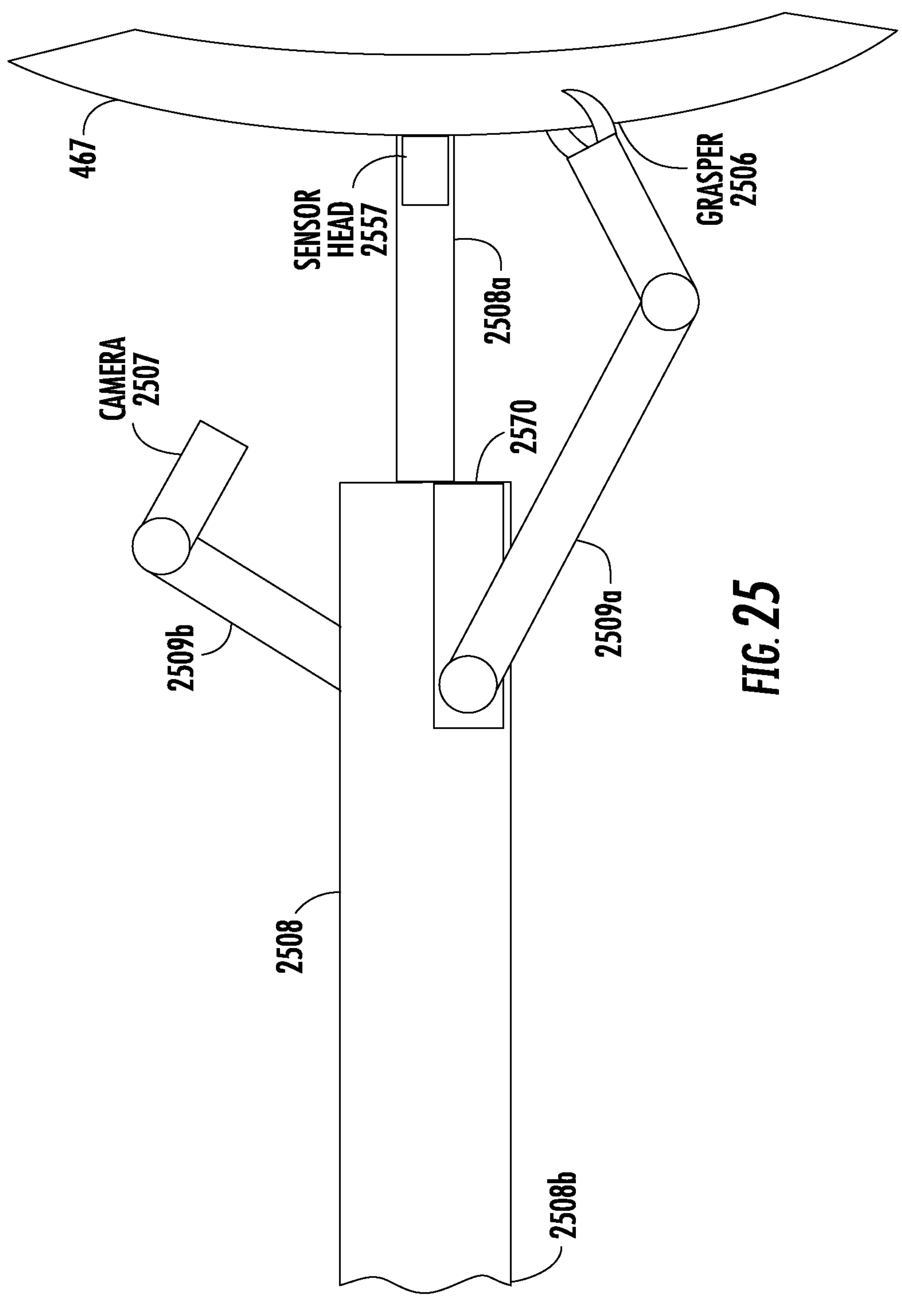
FIG. 25 shows an image of an end of a laparoscopic element that includes a grasper in an implementation.

FIG. 25 shows a diagram of a laparoscopic element 2508 in an implementation. The laparoscopic element is adapted to releasably connect or nonreleasably connect to one of the described probe units.

The laparoscopic element includes a sensor head 2557 positioned at a first end 2508*a* of the laparoscopic element. The laparoscopic element includes a grasper 2506 and a camera 2507. The laparoscopic element can include other surgical devices, such as a retractor (not shown). Control elements that are adapted to control the grasper and camera can be connected to a second end 2508*b* of laparoscopic element that is distally positioned with respect to first end 2508*a*. Portions of the control elements extend through the laparoscopic element to the surgical elements.

The grasper and camera can be respectively connected to the ends of control arms 2509*a* and 2509*b* that are connected to the laparoscopic element. The control arm can be articulated or otherwise be adapted to move the grasper and camera into positions for operation.

For example, control arm 2509*a* can be adapted to move the grasper into contact with tissue (e.g., intestinal tissue) 467 so that the grasper can grasp the tissue. When the grasper has grasped the tissue, the control arm can move the grasper so that the tissue moves into contact with the sensor head. Thereby, the sensor head can make oximetry measurements of the tissue.

Similarly, control arm 2509*b* can be configured to articulate such that the camera can be positioned to view the sensor head, such as from a side of the sensor head. Thereby, the camera can view the sensor head as the sensor head moves into contact with the tissue. Image information generated by the camera can be transmitted by transmitter 490 to tower mounted display 415 for display. A user of the oximeter system viewing the camera information can determine whether contact between the sensor head and the tissue is adequate for making oximetry measurements.

The two or more articulating portions of control arm 2509*a* can be adapted to "fold" onto each other for storage in a tool-storage channel 2570 that is formed in the laparoscopic element. Control arm 2509*b* can also be adapted to fold into a tool-storage channel (not shown) that can be oppositely positioned on the laparoscopic relative to tool-storage channel 2570. The articulating arms can also be adapted to retract into the laparoscopic element for storage where the arms are in a folded or nonfolded configuration.

Figure 26:
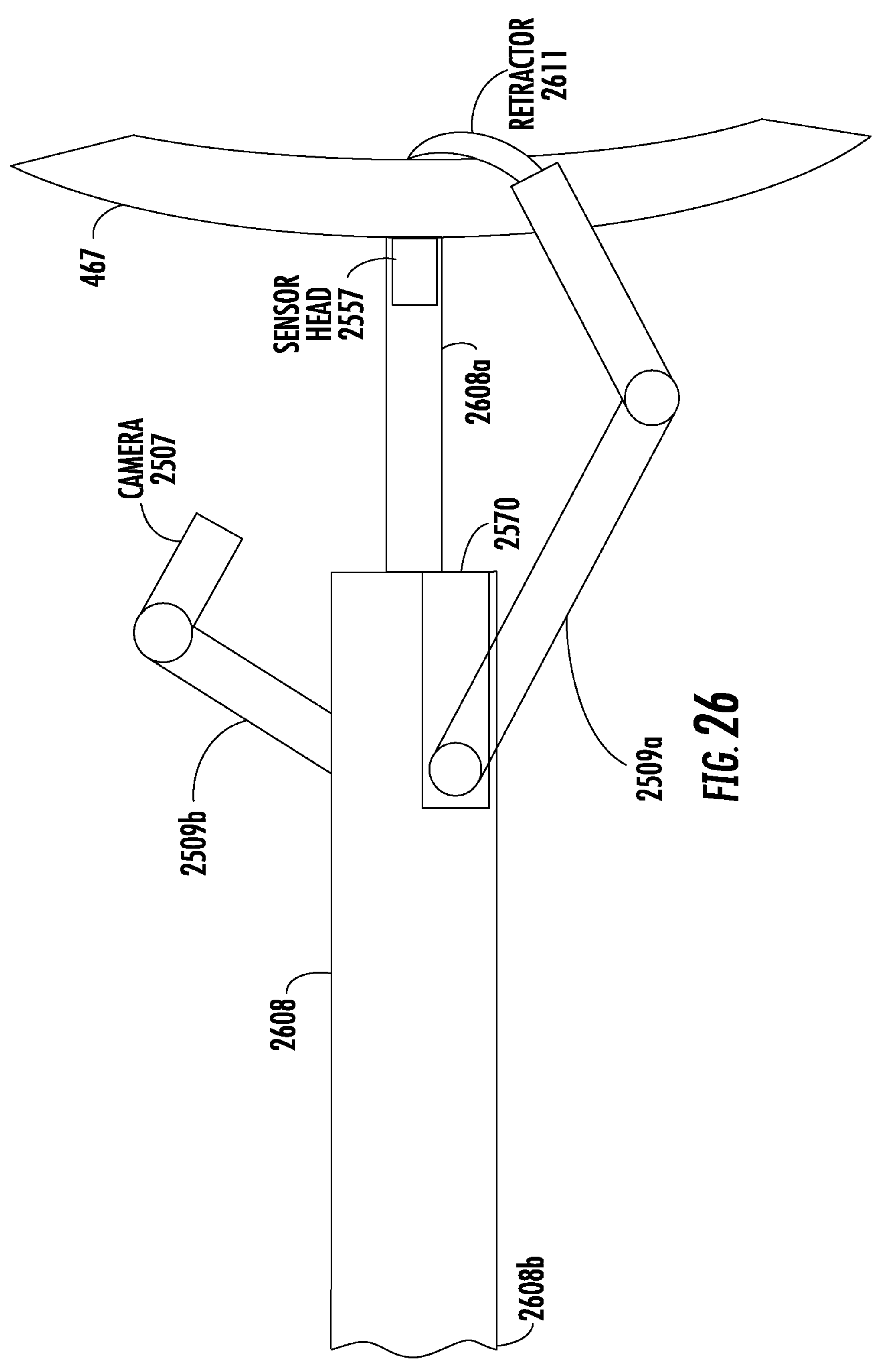
FIG. 26 shows an image of an end of a laparoscopic element that includes a retractor in an implementation.

FIG. 26 shows an image of a laparoscopic element 2608 in an implementation. The laparoscopic element is adapted to releasably connect or nonreleasably connect to one of the described probe units.

The laparoscopic element includes a sensor head 2557 positioned at a first end 2608*a* of the laparoscopic element. The laparoscopic element includes a retractor 2611 and camera 2507. The laparoscopic element can include other surgical devices, such as a grasper (not shown). Control elements that are adapted to control the retractor and camera can be connected to a second end 2608*b* of laparoscopic element. Portions of the control elements extend through the laparoscopic element to the surgical elements.

The retractor and camera can be respectively connected to the ends of control arms 2509*a* and 2509*b* that are connected to the laparoscopic element. The control arm can be articulated as described above with respect to FIG. 25 to move the retractor and camera into positions for operation.

For example, control arm 2509*a* can be adapted to move the retractor into contact with tissue (e.g., intestinal tissue) 467 so that the retractor can "hook" the tissue. When the retractor has hooked the tissue, the control arm can move the retractor so that the tissue can be retracted. In an implementation, the retractor can move the tissue into contact with the sensor head. Thereby the sensor head can make oximetry measurements of the tissue. Control arm 2509*b* can be configured to move the camera as described above with respect to FIG. 25. The control arms can be adapted to "fold" onto each other for storage in a tool-storage channel formed in the laparoscopic element.

Figure 27:
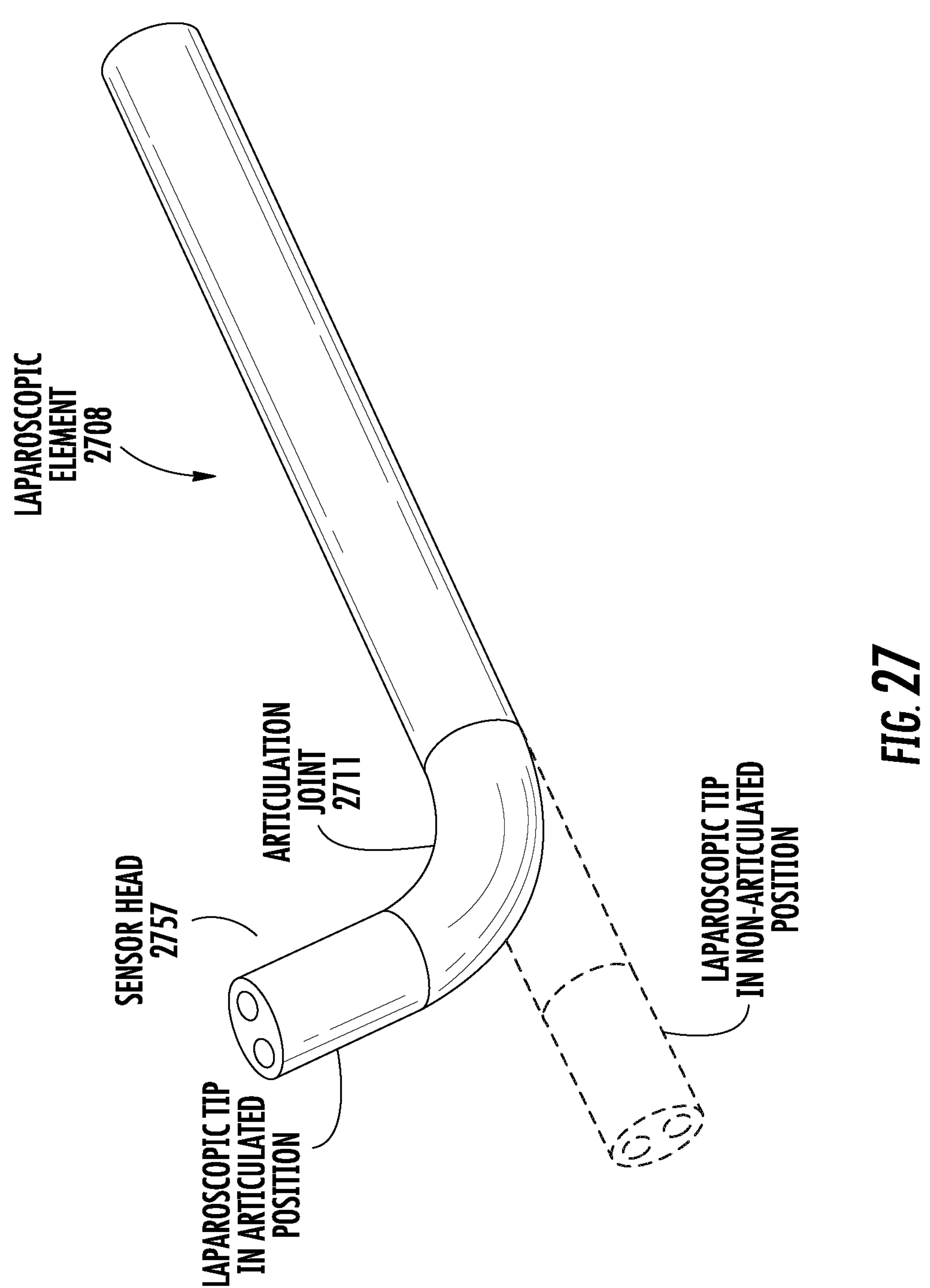
FIG. 27 shows a laparoscopic element where an end portion of the laparoscopic element is adapted to articulate at an articulation joint.

FIG. 27 shows a laparoscopic element 2708 where an end portion of the laparoscopic element is adapted to articulate about an articulation joint 2711. The end portion can have a sensor head 2757 that can be configured as described above. The laparoscopic element can be adapted to releasably connect to or nonreleasably connect to any of the described probe units. Control elements can be connected to the laparoscopic elements and be positioned in the element for controlling articulation of the articulation joint.

Figure 28:
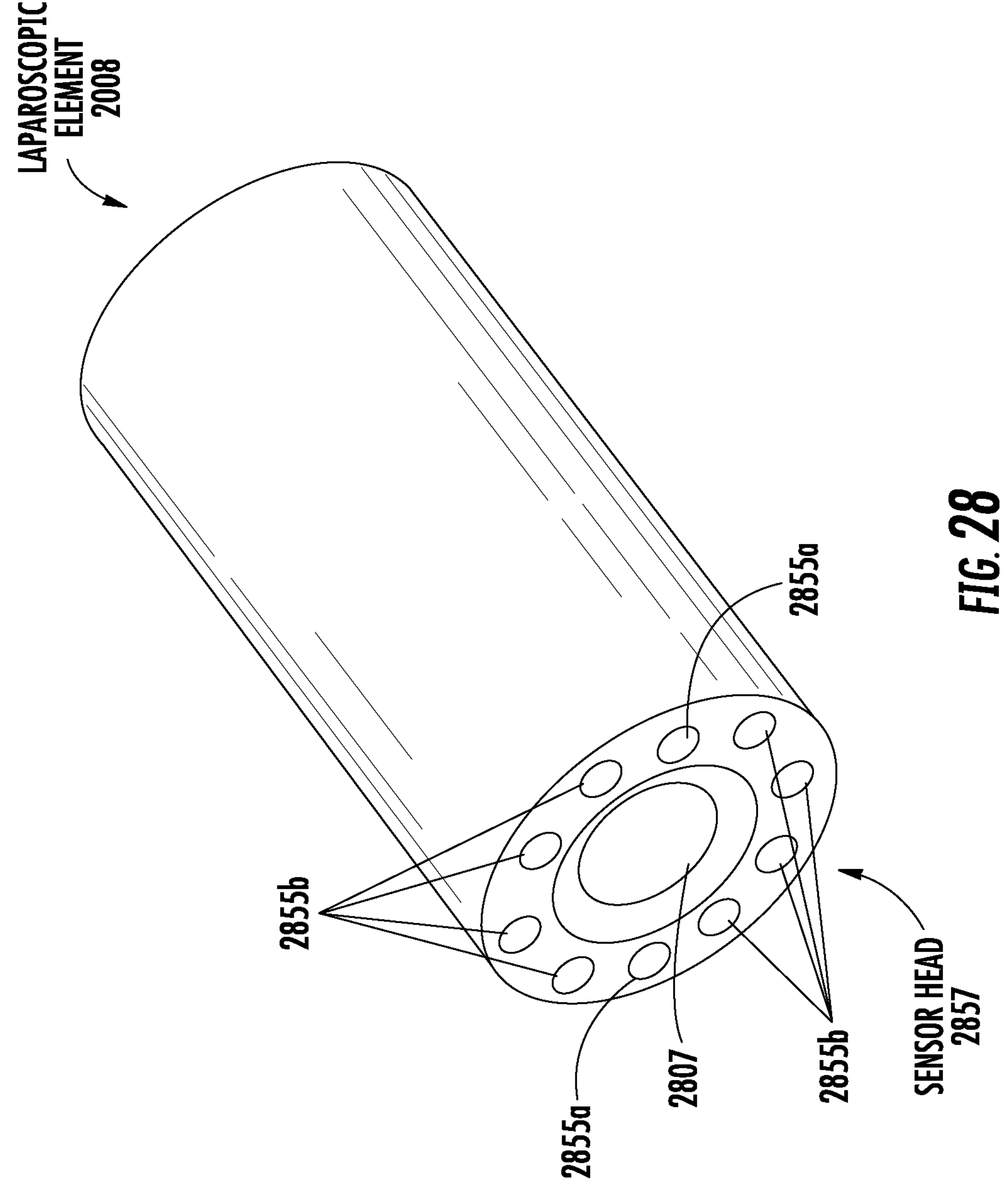
FIG. 28 shows an end view of a sensor head of a laparoscopic element that operates as a white light source for a camera and as a light source and detector for oximetry measurements.

FIG. 28 shows an end view of a sensor head 2857 of a laparoscopic element 2808 in an implementation. The laparoscopic element includes a camera 2807 positioned in the tube portion of the element. The laparoscopic element includes one or more source optical fibers 2855*a* and one or more source-detector optical fibers 2855*b* that extend through the laparoscopic element.

Each source optical fibers can transmit light from two different light sources. Specifically, each source optical fiber is optically connected to a light source, such as a white light. The white light source can be an LED. The each source optical fiber can transmit white light from the LED to tissue for illuminating the tissue for viewing by the camera. Each source optical fiber is also optically connected to light engine 440 to operate as a light source for oximetry measurements of the tissue.

Each source-detector optical fiber is adapted to operate as a light source and as a detector structure for collecting light. Specifically, each source-detector optical fiber is optically connected to a white light source. The white light source can be a white light LED or other light source. The source-detector optical fibers can transmit the white light to the tissue for illuminating the tissue for viewing by the camera.

Each source-detector optical fiber is also optically connected to one of the photodetectors 455. That is, each source-detector optical fiber is adapted to operate as a detector structure that collects light reflected from the tissue where the source optical fibers transmit light from the light engine to the tissue. That is, the source-detector optical fibers operate as light collectors for oximeter measurements.

While FIG. 28 shows that the sensor head includes two source optical fibers and eight source-detector optical fibers, the sensor head can include more or fewer source optical fibers, and more or fewer source-detector optical fibers. For example, the sensor head can include 1, 2, 3, 4, 5, 6, 7, 8, 9, 10, or more source optical fibers and 1, 2, 3, 4, 5, 6, 7, 8, 9, 10, or more source-detector optical fibers. The sensor head can include any one of these number of source optical fibers and source-detector optical fibers in any combination. For example, the sensor head can include one source optical fiber and two source-detector optical fibers, two source optical fibers and one source-detector optical fiber, two source optical fibers and two source-detector optical fiber, three source optical fibers and one source-detector optical fiber, three source optical fibers and two source-detector optical fibers, two source optical fibers and three source-detector optical fibers, or other combinations source optical fibers and source-detector optical fibers. These combinations of source optical fibers and source-detector optical fibers can have the spacing of sources and detectors shown in the table and described above.

Each source optical fiber 2855*a* that is optically connected to the white light source and the light engine can receive light from these sources via an end of the fiber, via a fiber optic coupler that directs light from the two sources into the fiber, via a beam splitter that is optically connected to the fiber, or by other optical devices.

Each source-detector optical fiber 2855*b* that is optically connected to the white light source and one of the photodetectors can receive light from the white light source via an end of the fiber, via a beam splitter that is optically connected to the fiber, or by other optical device. Light that is transmitted from the light engine into the tissue by the source optical fibers and that is collected by the source-detector optical fibers, can be directed from the source-detector optical fibers to the photodetectors from the ends of the fibers through which white light from the white light source is collected, via a beam splitter optically connected to the fiber and the photodetectors, or via other optical devices.

Figure 29:
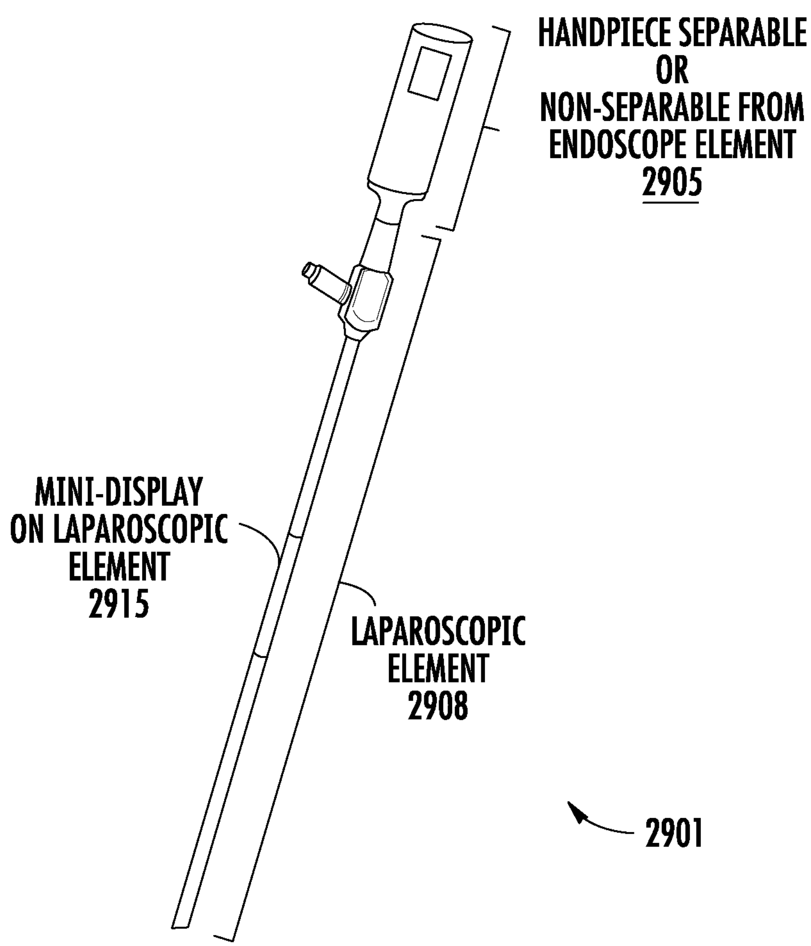
FIG. 29 shows as oximeter probe having a display located on the laparoscopic element of the probe.

FIG. 29 shows as oximeter probe 2901 in an implementation. The oximeter probe includes a probe unit 2905 and a laparoscopic element 2908. The oximeter probe can have one or more combinations of the optical and electrical components described above for oximeter probe 101, 401, 501, 601, 701, 1301, 1401, 1501, 1601, 1701, 1801, 1901, 2101, 2201, 2301, 2401, or other combinations of configurations of optical and electrical components. The laparoscopic element of the oximeter probe can be separable or nonseparable from the probe unit. The oximeter probe can have an integrated display or be adapted to use a separate display for displaying oximetry information.

The laparoscopic element includes a mini-display 2915 housed in the element where the mini-display is visible from outside of the element. The mini-display is electrically connected to processor 420 (not shown) that is housed in the probe unit or housed in a display 615 (hot shown). The processor is adapted to control the mini-display to display one or more pieces of oximetry information generated by the oximeter probe.

The mini-display can be positioned at a variety of lengths from the tip of the laparoscopic element such that the mini-display is visible when the laparoscopic element is inserted into a patient's abdomen for use, such as through a trocar.

The mini-display in this position allows for the mini-display to be in the field of view of a laparoscopic camera on a separate laparoscopic tool. The image information (e.g., video) generated by the camera can be displayed on the laparoscopic tower display. The laparoscopic tower display can be show a primary view of a surgical procedure being performed. Thereby, oximeter information displayed on the mini-display can be displayed on the laparoscopic tower display and adjacent to the portion of tissue being measured at the time. The display of the oximetry information on the laparoscopic tower display allows medical professionals to keep their eyes directed at the laparoscopic tower display during the surgery and not have to divert their eyes to the oximeter probe to see the oximetry information. The mini-display can be located at a variety of distances from the tip of the laparoscopic element, such as 5, 6, 7, 8, 9, 10, 11, 12, 13, 14, 15, 16, or more centimeters.

Image information (e.g., video) of a surgery that is generated by the camera can be stored in memory. With the mini-display in the field of view of the camera, the oximeter information is stored with the image information in memory. The recorded image information allows for the oximeter information to be retrieved for any given instant of a surgical procedure.

Figure 30:
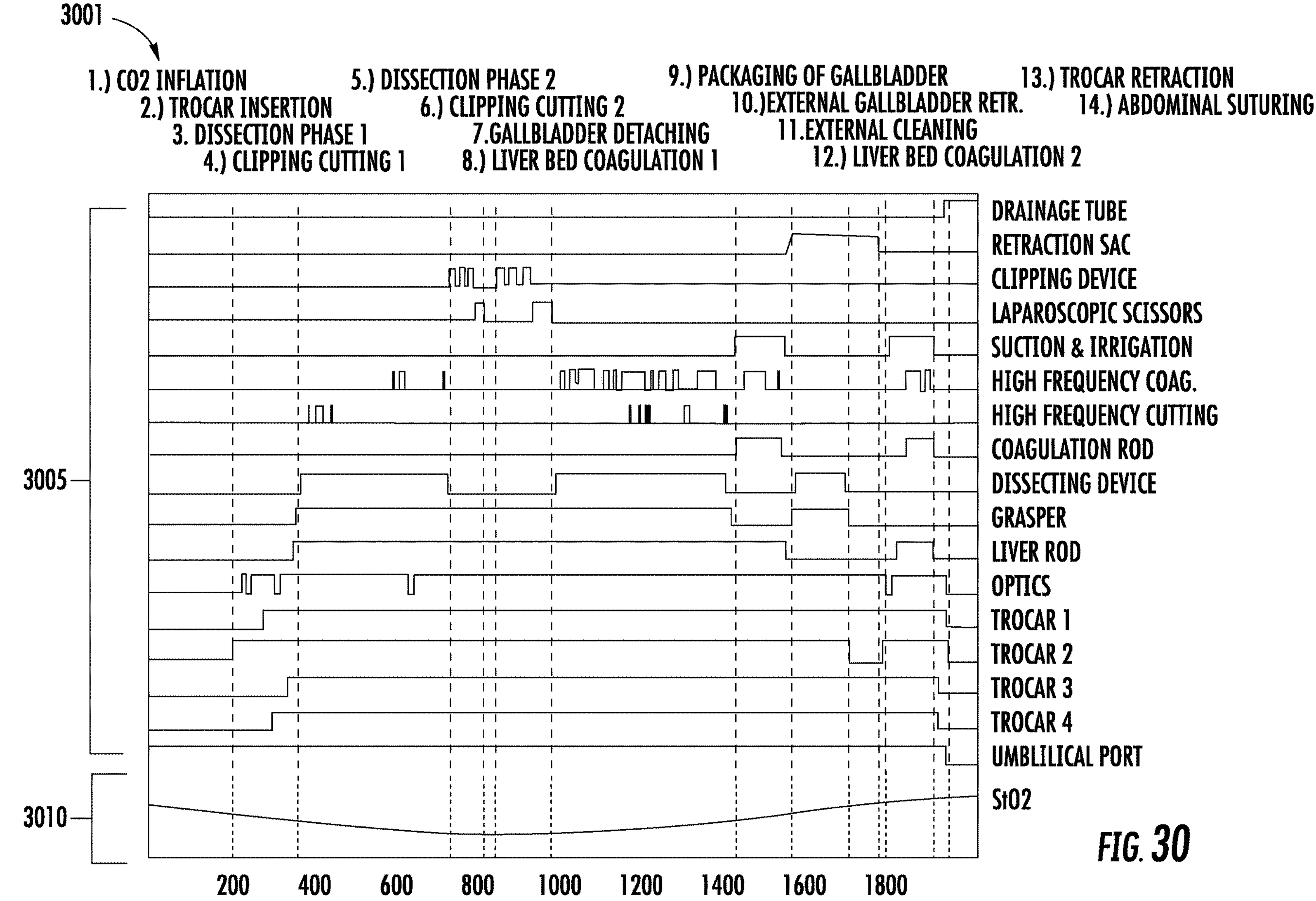
FIG. 30 shows an example status chart for a medial procedure in an implementation where an oximeter probe provides oximetry information included in the chart.

FIG. 30 shows an example status chart 3001 in an implementation. The chart includes information for a number of procedures that occur during a surgery performed on a patient and includes information for patient data. The chart can be presented on tower display 415, display 115 on an oximeter probe, or other display. The example status chart is specifically for a laparoscopic gallbladder removal from a patient. It will be understood that the chart is exemplary and will appear differently for other laparoscopic surgeries, such a large bowel resection, an appendectomy, or other surgery. The chart can also appear differently for medical procedures that are nonsurgical, such as a spinal tap.

The chart includes a number of procedure graphs (e.g., bar graphs) 3005 and includes one patient data graph 3010. The chart can include one or more additional patient data graphs. The graphs extend substantially horizontally across the chart from left to right. In the chart, time advances from left to right. For this example chart, the horizontal axis is divided into seconds. Other status charts might have horizontal axes that are divided into minutes.

Each procedure graph 3005 is associated with one procedure that occurs during the surgery and shows the times at which events occur in the procedures. The events that occur during a procedure are represented as binary steps along the graphs. For example, the graph for use of the grasper shows that the grasper was attached (first step-up in the graph) to tissue at 400 seconds into the procedure, was removed (first step-down in the graph) at 1400 seconds into the procedure, was attached (second step-up in the graph) again to tissue at 1500 seconds into the procedure, and then was removed (second-step down in the graph) a final time at 1600 seconds into the procedure. The other graphs, such as for the insertions and removals of the trocars, include similar step-ups (e.g., trocar insertions) and down steps (e.g., trocar removals) to indicate events that occur during the procedures during the surgery.

Patient data graph 3010 shows the oxygen saturation (StO2) for the patient's tissue being measured as the surgery progresses. The oxygen saturation can be for tissue in the patient's abdomen where the surgical procedure is taking place or can be for other tissue, such as skin or a skin flap. The information for the oxygen saturation can be provided to the display from one of the described oximeter probes that may be used during the surgery. The graph for oxygen saturation can represent absolute oxygen saturation or relative oxygen saturation. The graph can be displayed with one or more indicators (e.g., percentage indicators, numerical value, or other indicators) that indicate amounts of relative oxygen saturation change or absolute oxygen saturation information.

A status chart can include additional patient data graphs or graph 3010 can include alternative patient information. The additional or alternative patient data graphs can include information for total hemoglobin, blood volume, percentage of oxygenated hemoglobin, percentage of deoxygenated hemoglobin, melanin concentration, or other information.

In an implementation, information from one or more graphs shown in the status chart is saved in memory. The information can be saved in the memory of an oximeter probe, the tower display, or other device, such as a server to which the information is transmitted from the oximeter probe, the display, or an intermediary device. In an implementation, the stored information is stored in an electronic medical chart that is associated with the patient. The electronic medical chart can include additional information, such as medical history, about the patient. The electronic medical chart can be stored in a database where the database includes electronic medical charts for a number of patients.

Information from a status chart stored in the memory of an oximeter probe or the display can be retrieved via wired or wireless communication during or after a surgical procedure. Thereafter, the information can be stored in an electronic medical chart for the patient.

In an implementation, an oximeter probe is adapted to track movement of the sensor head during a medical procedure. For example, the oximeter probe is adapted to track the three-dimensional locations and movement of the sensor head in a patient's abdomen while a medical procedure is occurring. The oximeter probe can include one or more electrical devices to track absolute location or relative location of the sensor head as the sensor head is moved. The oximeter probe can include a gyroscopic device, a radio frequency location device (e.g., similar to a GPS receiver that receives information from a remote radio source), or other devices that collect location information.

The three-dimensional location information can be displayed in a graph on status chart 3001 and can be stored in memory as described above. The three-dimensional location information can be stored in an electronic medical chart in the memory for the patient.

This description of the invention has been presented for the purposes of illustration and description. It is not intended to be exhaustive or to limit the invention to the precise form described, and many modifications and variations are possible in light of the teaching above. Elements of the various implementations can be used with other implementations in a number of ways, such as combinations, substitutions, or both. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

The invention claimed is:

1. An oximeter device comprising: a first portion comprising an elongated tube, a sensor head comprising an emitter and a detector, wherein the sensor head is coupled to a distal end of the elongated tube, and an amplifier circuit located in an interior space of the elongated tube and coupled to the detector, and the detector comprises a light-to-electrical-current converter and is optically coupled to an opening of the first portion; and a second portion, coupled to a proximal end of the elongated tube, comprising a first wireless transceiver, wherein the second portion is electrically coupled to the first portion, wherein the first wireless transceiver is outside of the first portion.

2. The oximeter device of claim 1 wherein the detector is positioned distal to the emitter in the elongated tube.

3. A system comprising the oximeter device of claim 1 and comprising: a tablet device, comprising a second wireless transceiver, wherein the tablet device is wirelessly coupled to the oximeter device by way of the first wireless transceiver wirelessly coupling to the second wireless transceiver.

4. The system of claim 3 wherein the oximeter device receives light and the detector converts the light into digital signal information, and the oximeter device transmits the digital signal information wirelessly to the tablet device via the first wireless transceiver.

5. The system of claim 4 wherein the tablet device receives the digital signal information from the oximeter device via the second wireless transceiver, the tablet device processes the digital signal information using a processing circuit on the tablet device to obtain an oxygen saturation value, and the oxygen saturation value is displayed on the tablet device.

6. The system of claim 4 wherein to process the digital signal information using a processing circuit of the tablet device, the tablet device stores executable code to perform spatially resolved spectroscopy on the digital signal information and executes the executable code to calculate an oxygen saturation value using spatially resolved spectroscopy.

7. The oximeter device of claim 1 wherein the oximeter device comprises a first wired connector, which is outside of the first portion.

8. A system comprising the oximeter device of claim 7 and comprising: a tablet device, comprising a second wireless transceiver, wherein the tablet device is capable of being wirelessly coupled to the oximeter device by way of the first wireless transceiver wirelessly coupling to the second wireless transceiver, the oximeter device is capable of being coupled to the tablet device using a cable coupling the first wired connector to a second wired connector of the tablet device, and when the cable is used to connect the oximeter device to the tablet device, a wireless link between the oximeter device and tablet device is disabled, and digital signal information from the oximeter device is transmitted by the cable from the oximeter device to the tablet device.

9. The oximeter device of claim 1 wherein the oximeter device comprises a battery as a power source for the first wireless transceiver.

10. The oximeter device of claim 9 wherein the battery is a power source for the emitter.

11. The oximeter device of claim 1 wherein the elongated tube comprises a first cross-section transverse to a longitudinal direction of the elongated tube, and the first cross-section comprises a first length, and the first wireless transceiver comprises a second cross-section having a second length that is larger than the first length.

12. The oximeter device of claim 1 wherein the sensor head is coupled to an opening at the distal end of the elongated tube.

13. The oximeter device of claim 12 wherein the elongated tube comprises a uniform diameter along a longitudinal direction between the proximal and distal ends.

14. The oximeter device of claim 12 wherein the sensor head comprises a surface that is transverse to a longitudinal direction of the elongated tube, the emitter is positioned on the sensor head, and the emitter emits light in the longitudinal direction and in a direction away from the surface of the sensor head and away from the proximal end.

15. The oximeter device of claim 12 wherein the detector is positioned on the sensor head, wherein the detector faces the opening at the distal end of the elongated tube.

16. The oximeter device of claim 12 wherein the amplifier circuit is coupled to the detector closer to the distal end than the proximal end of the elongated tube.

17. The oximeter device of claim 12 wherein the elongated tube is metal.

18. The oximeter device of claim 17 wherein the metal is stainless steel.

19. The oximeter device of claim 12 wherein the elongated tube is flexible.

20. An oximeter device comprising: a first portion, comprising an elongated tube, an amplifier circuit located in an interior space of the elongated tube, an oximeter sensor, wherein the oximeter sensor comprises an emitter and a detector, and the detector is coupled to the amplifier circuit and comprises a light-to-electrical-current converter and is optically coupled to an opening of the first portion; and a second portion, comprising a first wireless transceiver, coupled to the oximeter sensor, wherein the first wireless transceiver is outside of the first portion.

21. A system comprising the oximeter device of claim 20 and comprising: a tablet device, comprising a second wireless transceiver, wherein the tablet device is wirelessly coupled to the oximeter device by way of the first wireless transceiver wirelessly coupling to the second wireless transceiver.

22. The system of claim 21 wherein the oximeter device receives light and the detector converts the light into digital signal information, and the oximeter device transmits the digital signal information wirelessly to the tablet device via the first wireless transceiver.

23. The system of claim 22 wherein the tablet device receives the digital signal information from the oximeter device via the second wireless transceiver, the tablet device processes the digital signal information using a processing circuit of the tablet device to obtain an oxygen saturation value, and the oxygen saturation value is displayed on the tablet device.

24. The oximeter device of claim 20 wherein the elongated tube is metal.

25. The oximeter device of claim 24 wherein the metal is stainless steel.

26. The oximeter device of claim 20 wherein the elongated tube is flexible.

27. A device comprising: an elongated tube, comprising a proximal end and a distal end, wherein the elongated tube comprises a uniform diameter along a longitudinal direction between the proximal and distal ends, and an opening is at the distal end; a sensor head, coupled to the opening at the distal end of the elongated tube, wherein the sensor head comprises a surface that is transverse to the longitudinal direction; an emitter, positioned on the sensor head, wherein the emitter emits light in the longitudinal direction and in a direction away from the surface of the sensor head and away from the proximal end; a detector, positioned on the sensor head, wherein the detector comprises a light-to-electrical-current converter and faces the opening at the distal end of the elongated tube; and an amplifier circuit, positioned within an interior tubular space of the elongated tube, wherein the amplifier circuit is coupled to the detector closer to the distal end than the proximal end of the elongated tube.

28. The device of claim 27 wherein the device is an oximeter.

29. The device of claim 27 wherein the detector is positioned distal to the emitter in the elongated tube.

30. The device of claim 27 wherein the device comprises a first wired connector, which is outside of the elongated tube.

31. The device of claim 27 wherein the elongated tube comprises stainless steel.

32. The device of claim 27 wherein the device processes digital signal information using a processing circuit of a system unit of the device, the system unit stores executable code to perform spatially resolved spectroscopy on the digital signal information and executes the executable code to calculate an oxygen saturation value using spatially resolved spectroscopy.

33. The device of claim 27 wherein the elongated tube is metal.

34. The device of claim 33 wherein the metal is stainless steel.

35. The device of claim 27 wherein the elongated tube is flexible.

* * * * *